(12) United States Patent
Shimoyama

(10) Patent No.: US 10,064,748 B2
(45) Date of Patent: Sep. 4, 2018

(54) STENT DELIVERY SYSTEM

(71) Applicant: TERUMO KABUSHIKI KAISHA, Tokyo (JP)

(72) Inventor: Masakazu Shimoyama, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 260 days.

(21) Appl. No.: 15/003,101

(22) Filed: Jan. 21, 2016

(65) Prior Publication Data

US 2016/0135975 A1 May 19, 2016

Related U.S. Application Data

(63) Continuation of application No. PCT/JP2014/065238, filed on Jun. 9, 2014.

(30) Foreign Application Priority Data

Jul. 22, 2013 (JP) ................................. 2013-151717
Jul. 22, 2013 (JP) ................................. 2013-151721

(51) Int. Cl.
| | | |
|---|---|---|
| *A61F 2/966* | (2013.01) | |
| *A61F 2/86* | (2013.01) | |
| *A61F 2/844* | (2013.01) | |
| *A61F 2/852* | (2013.01) | |
| *A61F 2/95* | (2013.01) | |

(52) U.S. Cl.
CPC .............. *A61F 2/966* (2013.01); *A61F 2/844* (2013.01); *A61F 2/852* (2013.01); *A61F 2/86* (2013.01); *A61F 2002/9517* (2013.01)

(58) Field of Classification Search
CPC .. A61F 2/95; A61F 2/962; A61F 2/966; A61F 2002/9517; A61F 2002/9522
See application file for complete search history.

(56) References Cited

U.S. PATENT DOCUMENTS 5,501,654 A * 3/1996 Failla ................. A61B 17/0218
600/204
6,866,669 B2 * 3/2005 Buzzard .................... A61F 2/95
606/108

(Continued)

FOREIGN PATENT DOCUMENTS

| JP | 2007-504897 A | 3/2007 |
|---|---|---|
| JP | 2012-513878 A | 6/2012 |

(Continued)

OTHER PUBLICATIONS

International Search Report (PCT/ISA/210) dated Sep. 9, 2014, by the Japanese Patent Office as the International Searching Authority for International Application No. PCT/JP2014/065238.

*Primary Examiner* — Ryan J Severson
(74) *Attorney, Agent, or Firm* — Buchanan Ingersoll & Rooney PC

(57) ABSTRACT

A stent delivery system is disclosed in which a stent is contained in a sheath in an initial state and the stent is released inside a living body lumen in accordance with a movement of the sheath in a proximal direction with respect to an inner member. A movement mechanism of the stent delivery system has a rack member which is connected to a proximal end of the sheath, and a plurality of pinions which move the rack member in accordance with rotations thereof.

20 Claims, 15 Drawing Sheets

(56) References Cited

U.S. PATENT DOCUMENTS

| | | | | |
|---|---|---|---|---|
| 7,052,511 B2* | 5/2006 | Weldon | A61F 2/95 | 606/194 |
| 7,326,236 B2* | 2/2008 | Andreas | A61F 2/95 | 623/1.11 |
| 7,758,625 B2* | 7/2010 | Wu | A61F 2/95 | 623/1.11 |
| 7,935,141 B2* | 5/2011 | Randall | A61F 2/95 | 606/108 |
| 7,967,829 B2* | 6/2011 | Gunderson | A61F 2/95 | 606/108 |
| 7,976,574 B2* | 7/2011 | Papp | A61F 2/95 | 623/1.11 |
| 8,366,760 B2* | 2/2013 | Kumoyama | A61F 2/95 | 623/1.11 |
| 8,585,752 B2* | 11/2013 | Sudo | A61F 2/91 | 623/1.15 |
| 8,657,869 B2* | 2/2014 | Moberg | A61F 2/95 | 623/1.12 |
| 8,702,778 B2* | 4/2014 | Loewen | A61F 2/95 | 623/1.11 |
| 8,702,783 B2* | 4/2014 | Yamashita | A61F 2/95 | 623/1.11 |
| 8,888,833 B2* | 11/2014 | Molloy | A61F 2/95 | 623/1.11 |
| 9,039,750 B2* | 5/2015 | Ryan | A61F 2/966 | 623/1.11 |
| 9,452,071 B2* | 9/2016 | Shimoyama | A61F 2/966 | |
| 9,492,298 B2* | 11/2016 | Shimoyama | A61F 2/966 | |
| 9,539,130 B2* | 1/2017 | Farag | A61F 2/966 | |
| 9,615,949 B2* | 4/2017 | Ryan | A61F 2/95 | |
| 9,662,235 B2* | 5/2017 | Munsinger | A61F 2/95 | |
| 9,662,236 B2* | 5/2017 | Masubuchi | A61F 2/962 | |
| 9,707,115 B2* | 7/2017 | Masakazu | A61F 2/966 | |
| 9,820,876 B2* | 11/2017 | Cummins | A61F 2/966 | |
| 2003/0191516 A1* | 10/2003 | Weldon | A61F 2/95 | 623/1.12 |
| 2004/0006380 A1* | 1/2004 | Buck | A61F 2/966 | 623/1.11 |
| 2004/0193180 A1* | 9/2004 | Buzzard | A61F 2/95 | 606/108 |
| 2005/0060016 A1 | 3/2005 | Wu et al. | | |
| 2005/0080476 A1* | 4/2005 | Gunderson | A61F 2/95 | 623/1.11 |
| 2005/0149159 A1* | 7/2005 | Andreas | A61F 2/95 | 623/1.11 |
| 2005/0273151 A1* | 12/2005 | Fulkerson | A61F 2/966 | 623/1.11 |
| 2005/0288763 A1* | 12/2005 | Andreas | A61F 2/95 | 623/1.11 |
| 2005/0288764 A1* | 12/2005 | Snow | A61F 2/95 | 623/1.11 |
| 2005/0288766 A1* | 12/2005 | Plain | A61F 2/95 | 623/1.12 |
| 2007/0060999 A1* | 3/2007 | Randall | A61F 2/95 | 623/1.11 |
| 2007/0088421 A1* | 4/2007 | Loewen | A61F 2/95 | 623/1.11 |
| 2008/0188920 A1* | 8/2008 | Moberg | A61F 2/95 | 623/1.12 |
| 2010/0036472 A1* | 2/2010 | Papp | A61F 2/95 | 623/1.11 |
| 2010/0076541 A1* | 3/2010 | Kumoyama | A61F 2/95 | 623/1.11 |
| 2010/0125280 A1* | 5/2010 | Molloy | A61F 2/95 | 606/108 |
| 2010/0168834 A1 | 7/2010 | Ryan et al. | | |
| 2012/0022635 A1* | 1/2012 | Yamashita | A61F 2/95 | 623/1.12 |
| 2012/0116493 A1* | 5/2012 | Harada | A61F 2/95 | 623/1.12 |
| 2012/0209366 A1* | 8/2012 | Sudo | A61F 2/91 | 623/1.11 |
| 2012/0330401 A1* | 12/2012 | Sugimoto | A61F 2/915 | 623/1.12 |
| 2013/0184805 A1* | 7/2013 | Sawada | A61F 2/97 | 623/1.11 |
| 2013/0268049 A1* | 10/2013 | Munsinger | A61F 2/95 | 623/1.11 |
| 2013/0304189 A1* | 11/2013 | Shimoyama | A61F 2/966 | 623/1.12 |
| 2014/0025155 A1 | 1/2014 | Masubuchi | | |
| 2014/0257459 A1* | 9/2014 | Masakazu | A61F 2/966 | 623/1.11 |
| 2014/0343660 A1* | 11/2014 | Shimoyama | A61F 2/966 | 623/1.11 |
| 2015/0265445 A1* | 9/2015 | Weber | A61F 2/966 | 623/1.12 |
| 2016/0135975 A1* | 5/2016 | Shimoyama | A61F 2/844 | 623/1.12 |

FOREIGN PATENT DOCUMENTS

| | | |
|---|---|---|
| JP | 2012-187177 A | 10/2012 |
| WO | WO 2005/032614 A2 | 4/2005 |
| WO | WO 2012/132508 A1 | 10/2012 |

* cited by examiner

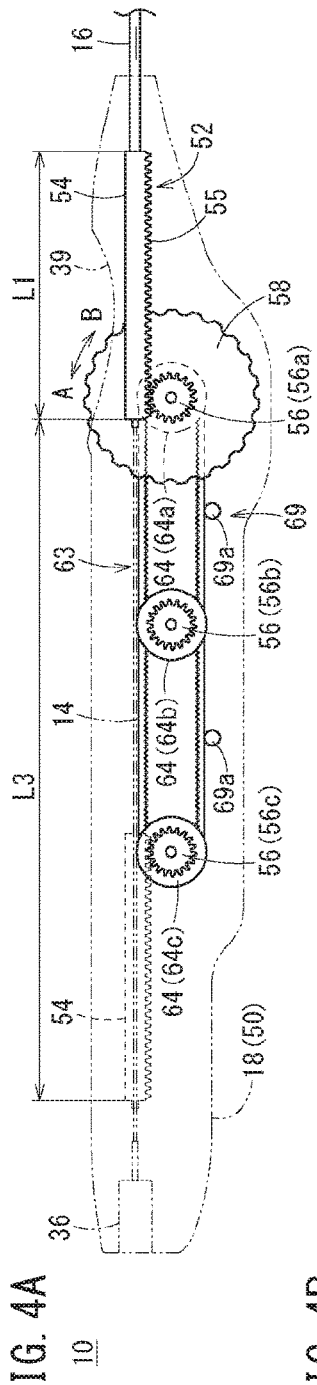
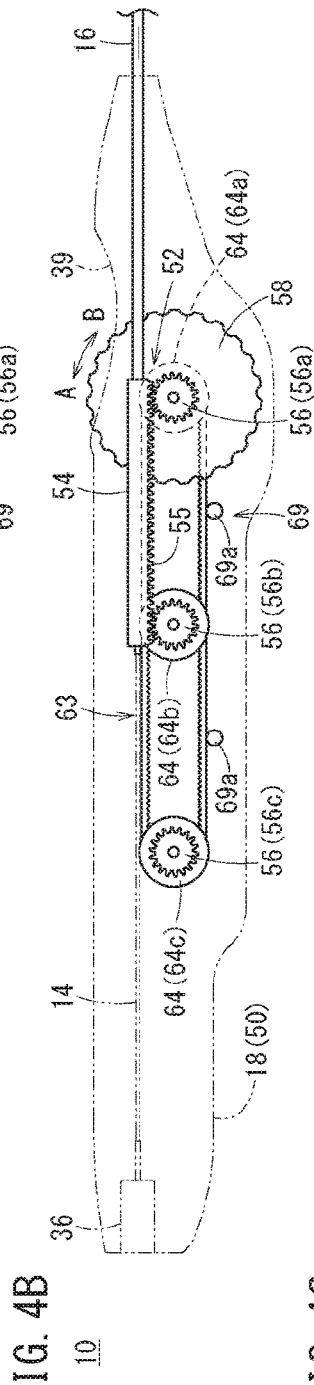
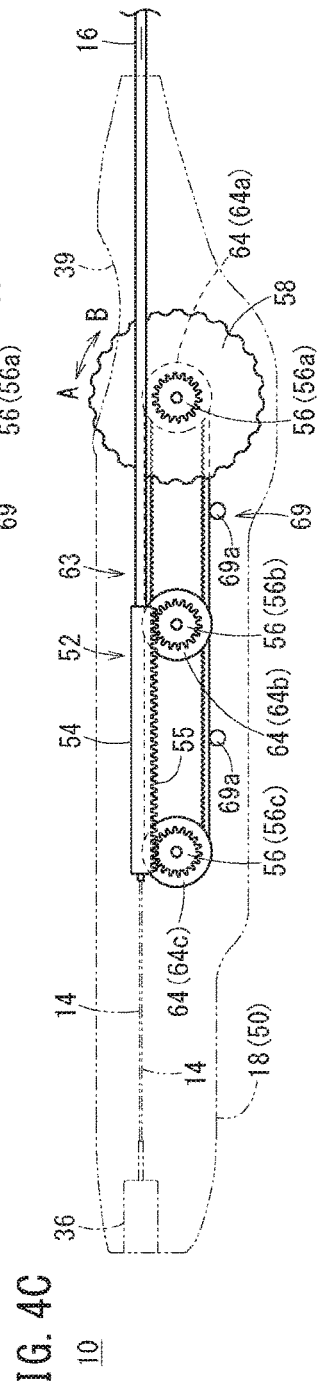
FIG. 4A
FIG. 4B
FIG. 4C

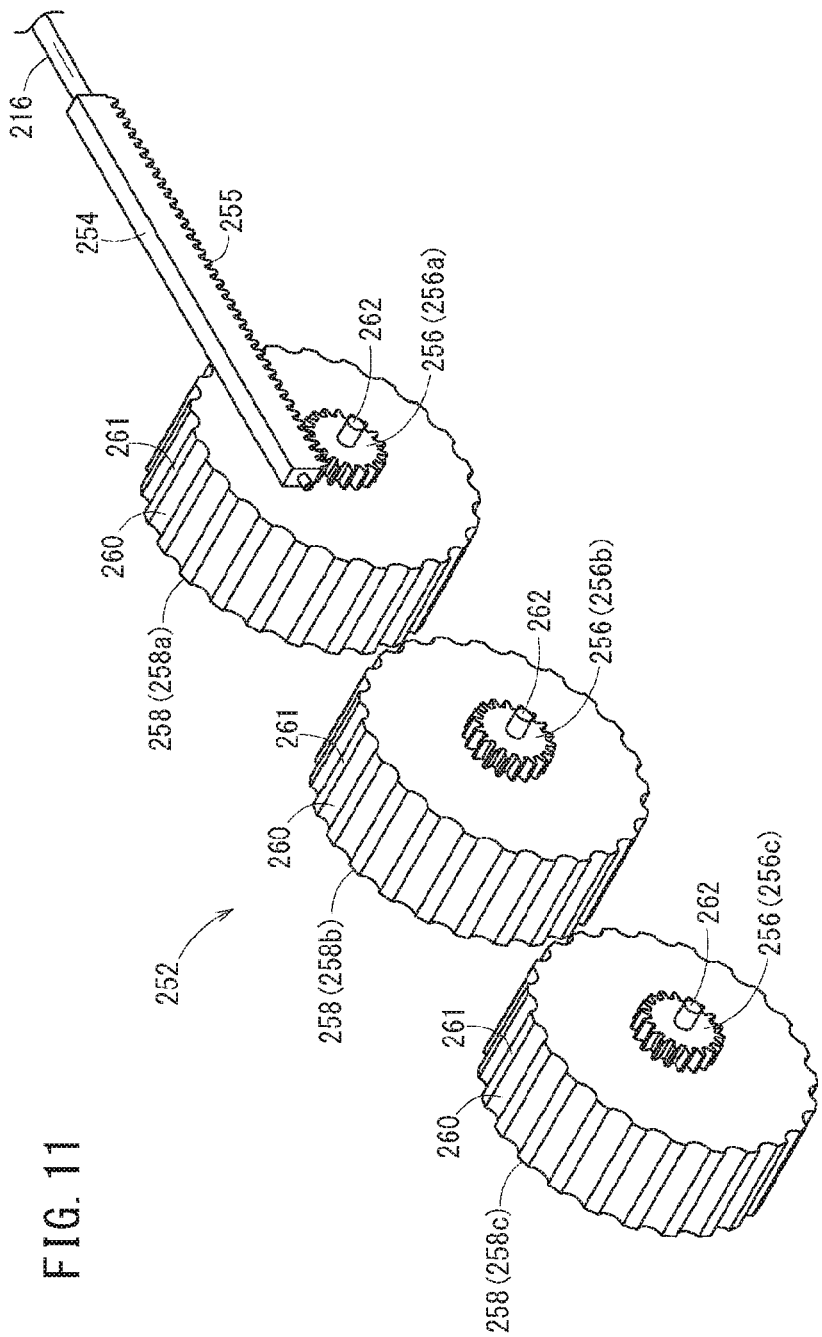

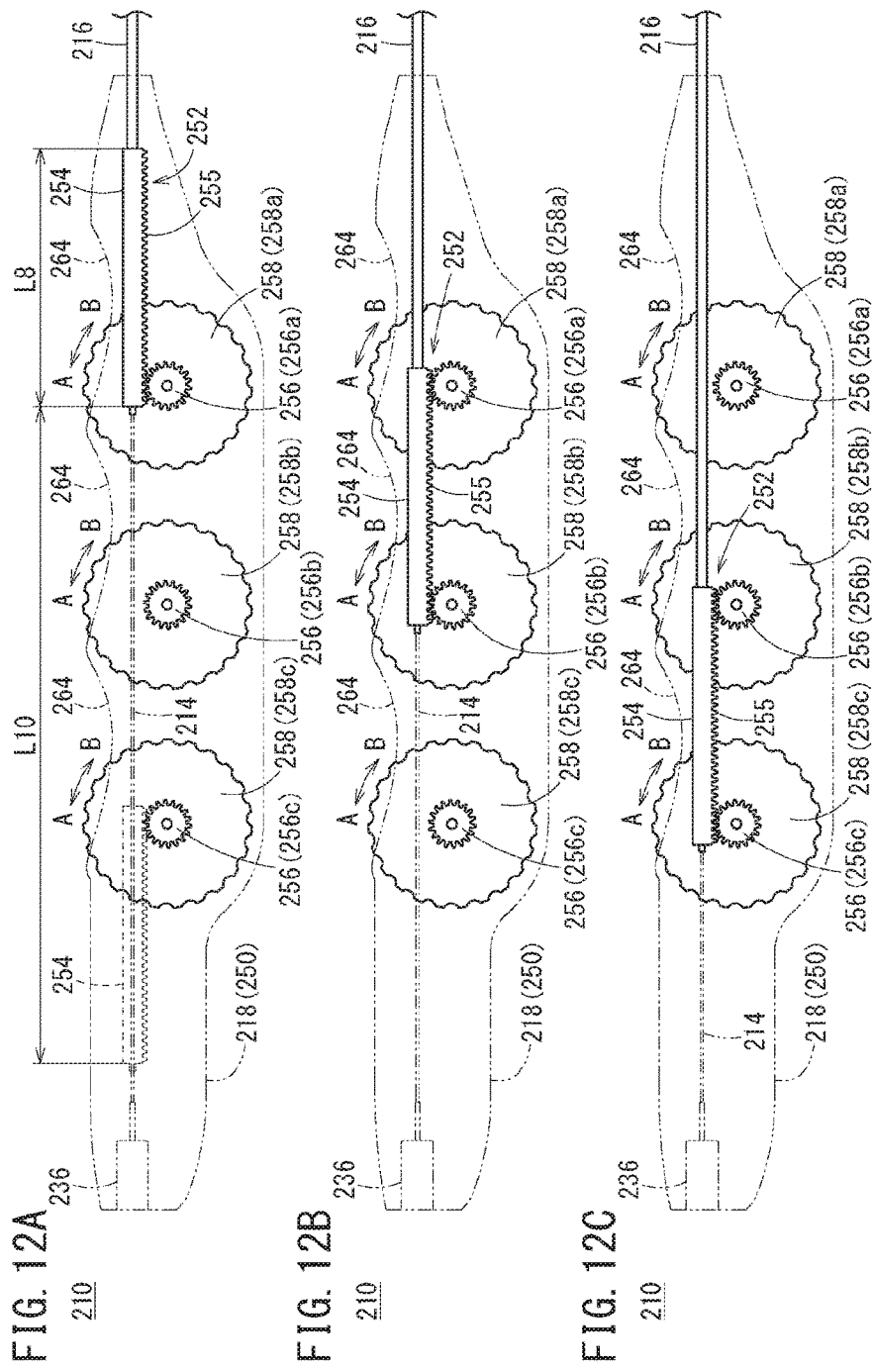

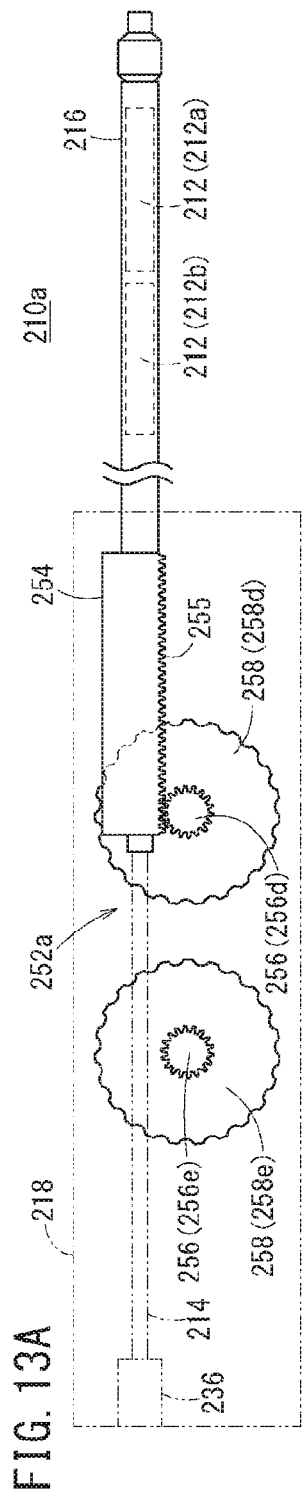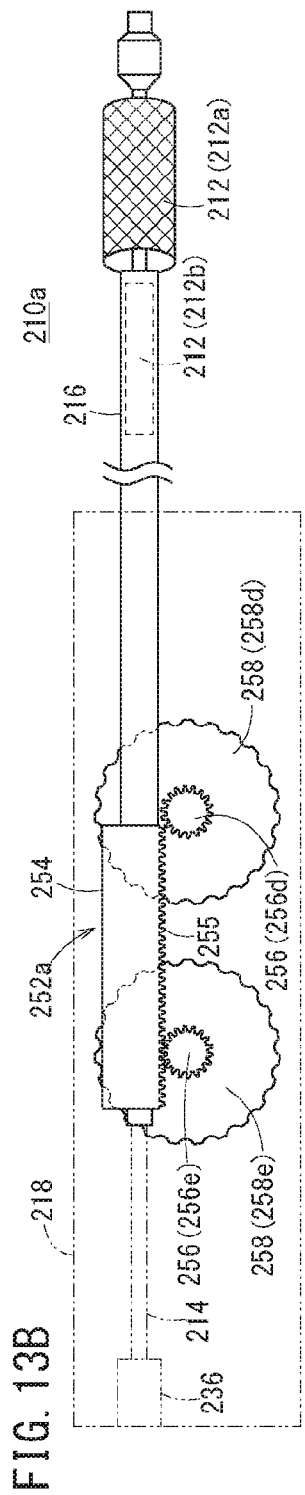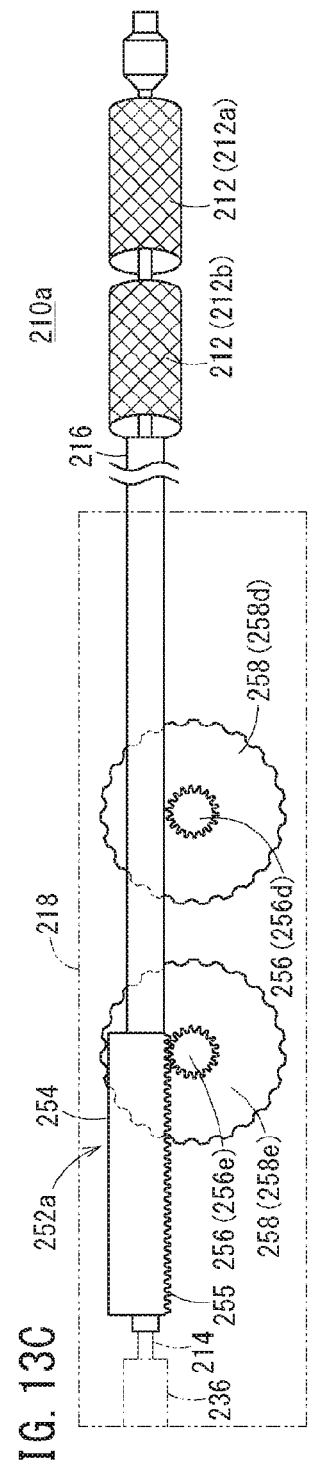

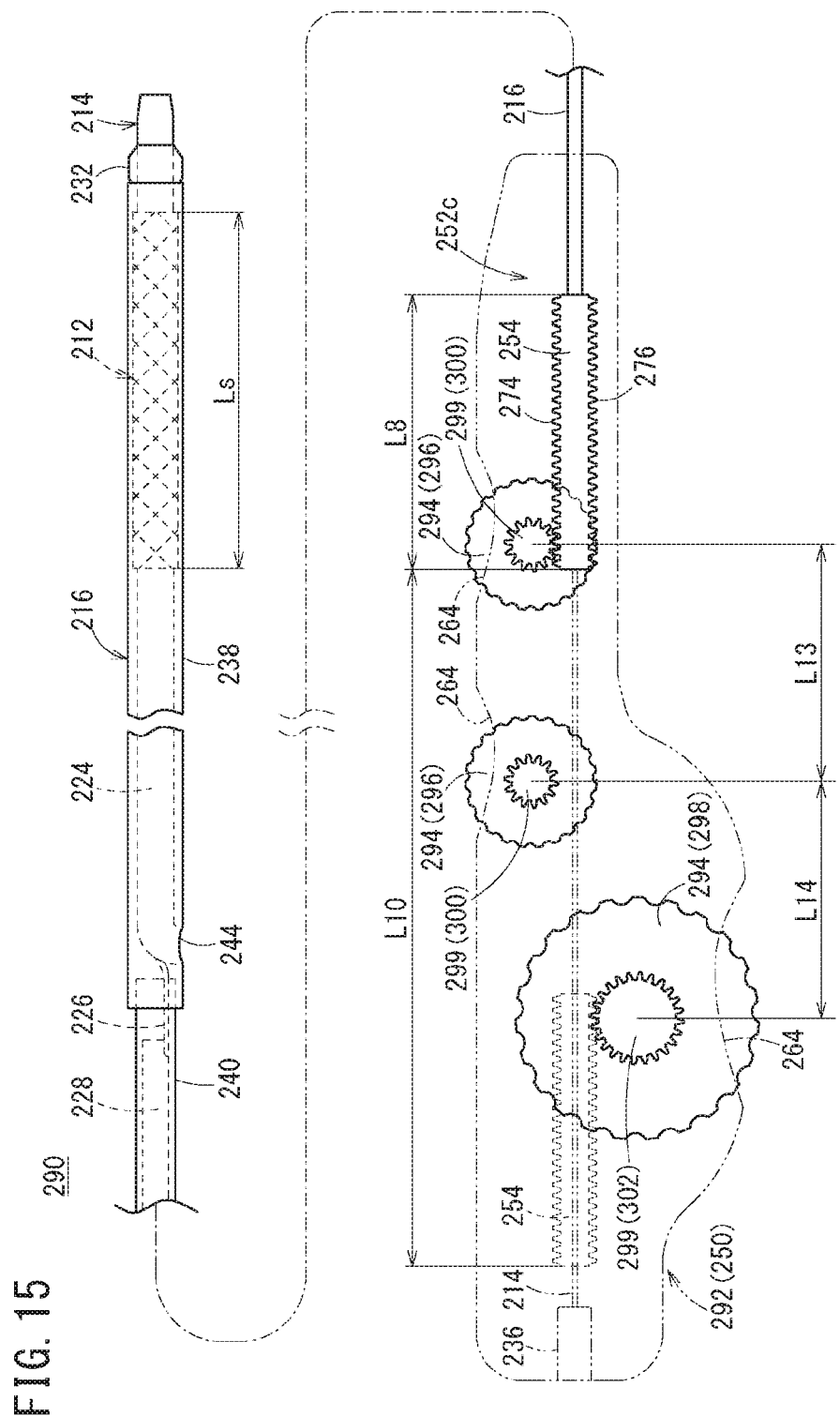

STENT DELIVERY SYSTEM

CROSS-REFERENCES TO RELATED APPLICATIONS

This application is a continuation of International Application No. PCT/JP2014/065238 filed on Jun. 9, 2014, and claims priority to Japanese Application No. 2013-151717 and 2013-151721 filed on Jul. 22, 2013, the entire contents of which are incorporated herein by reference.

TECHNICAL FIELD

The present disclosure generally relates to a stent delivery system in which a stent is delivered to the inside of a living body lumen such as a blood vessel and the like and indwells therein.

BACKGROUND DISCUSSION

Conventionally, a stent is applied in order to improve a stenosed site or an obstructive site which has occurred inside a living body lumen such as a blood vessel, the bile duct, the trachea, the esophagus, urethra, and the like. The stent is formed with a metal wire and the like, has a cylindrical shape in its entirety, is configured to have multiple side wall openings, and is expandable in a living body lumen.

As a type of the stent, there is a balloon expandable stent, which is mounted on a balloon of a balloon catheter and indwells in a living body lumen by being widened from the inner side by the balloon. In addition, another type of the stent, is a self-expandable stent which is provided with a function of self-expansion conducted by elastic force and indwells in a living body lumen by being released from a sheath or the like in the living body lumen and conducting self-expansion. A stent delivery system is applied in order to deliver the balloon expandable stent or the self-expandable stent to a desired position inside a living body lumen and to indwell the stent therein.

Generally, a stent delivery system having a conventional self-expandable stent includes an inner tube, a stent that is mounted outside the inner tube in the vicinity of a distal end portion thereof, an outer tube that is displaceable in an axial direction outside the inner tube and accommodates the stent in a contracted state, and a grip that is connected to a proximal end portion of the outer tube. In a procedure in which the stent delivery system is applied, the stent is delivered to the inside of a living body lumen in a state of being compressed and contained in an aperture between the inner tube and the outer tube, and the stent is released and indwells in the living body lumen by moving the outer tube in a proximal direction with respect to the inner tube.

In the stent delivery system, a movement mechanism for causing the outer tube to relatively move in the axial direction with respect to the inner tube is further provided in the grip. The movement mechanism has a rotatable operation wheel and a rack member, which is provided with a rack that meshes with a pinion provided in the operation wheel. Then, the proximal end portion of the outer tube is connected to the rack member. When the operation wheel of the aforementioned movement mechanism rotates in a predetermined direction, the rack member moves rearward and the outer tube thereby moves rearward with respect to the inner tube in accordance with a movement thereof. Thus, the stent is released from the outer tube to the inside of a living body lumen. JP-T-2007-504897 discloses a conventional stent delivery system, for example.

Stents can also have a long overall length (for example, equal to or greater than 20 cm) in accordance with a site to be treated. In addition, a plurality of stents can be arranged side by side in an axial direction of an inner tube and the plurality of stents can be released and indwelled in a living body lumen. In order to release a stent having the long overall length or a plurality of stents inside a living body lumen, a movement distance of a rack member in a proximal direction from the initial position needs to be elongated. In a conventional stent delivery system, since the rack member is configured to be moved by one pinion, the rack member requires an overall length corresponding to a necessary movement distance in order to move the rack member rearward as far as the necessary movement distance. Then, since the rack member is arranged so as to extend from the pinion side in a distal direction at the initial position, a grip is required to extend in the distal direction in accordance with the length of the rack member. As a result thereof, there is an occurrence of a problem in that the overall length of the grip is elongated and the tractability thereof during a procedure can deteriorate.

SUMMARY

A stent delivery system is disclosed in which a stent can be released and indwell in a living body lumen without elongating the overall length of a grip even when a stent having the quite long overall length or a plurality of stents are applied.

A stent delivery system is disclosed, which can include an inner member, a sheath that is arranged outside the inner member so as to be movable in an axial direction with respect to the inner member, a self-expandable stent that is arranged between the inner member and the sheath, and a grip that includes a movement mechanism for moving the sheath in the axial direction with respect to the inner member. The stent is contained in the sheath in an initial state, and the stent is released inside a living body lumen in accordance with a movement of the sheath in a proximal direction with respect to the inner member. The movement mechanism has a displacement member which is connected to the sheath, which is movable along the axial direction of the stent delivery system, and which extends in the axial direction, and a plurality of driving rotators which are arranged at intervals from each other in an extension direction of the displacement member, and move the displacement member in the extension direction in accordance with rotations thereof.

According to the stent delivery system, the displacement member continuously moves in the proximal direction by the plurality of driving rotators which are provided at intervals from each other along the extension direction of the displacement member. According to the aforementioned configuration, the overall length of the displacement member can be shortened compared to that in a configuration in which the displacement member is moved by one driving rotator. Thus, even in a case of a configuration having a long stent or a plurality of stents arranged side by side in the axial direction to be released, the movement distance required for the displacement member can be ensured without elongating the overall length of the displacement member. Therefore, the length of the grip can be curtailed up to the shortened length of the displacement member and the tractability of the grip during a procedure can be improved.

In the stent delivery system, an interlocking mechanism is disclosed, which interlocks the plurality of driving rotators with each other and a rotative operation portion which rotates the plurality of driving rotators via the interlocking mechanism. According to the aforementioned configuration, since remaining driving rotators are configured to rotate while being interlocked with rotations of one driving rotator, the total number of the rotative operation portions may be smaller than the total number of the driving rotators so that the stent delivery system is simply operated.

In the stent delivery system, one of the plurality of driving rotators may be provided in the rotative operation portion. According to the aforementioned configuration, the plurality of driving rotators can be reliably interlocked with each other in a relatively simple structure.

In the stent delivery system, the interlocking mechanism may have a plurality of rotative portions which are coaxially and respectively provided in the plurality of driving rotators, and at least one transmission member which comes into contact with the plurality of rotative portions so as to be able to transmit power thereto. According to the aforementioned configuration, the plurality of driving rotators can be reliably interlocked with each other in simple structure.

In the stent delivery system, when the plurality of rotative portions are interlocked with each other by the transmission member, the rotative portion on the farthest proximal side may rotate faster than the rotative portion on the farthest distal side. According to the aforementioned configuration, the stent can be relatively easily positioned at the initial stage of release by releasing the stent relatively slowly, and a procedure can finish early at the end stage of release by releasing the stent relatively quickly.

In the stent delivery system, the plurality of driving rotators may include a plurality of the first driving rotators and a plurality of the second driving rotators. At least one of the first driving rotators and at least one of the second driving rotators may be able to drive the displacement member at all times within a movable range of the displacement member. The interlocking mechanism may have a first interlocking portion, which interlocks the plurality of first driving rotators with each other, and a second interlocking portion, which interlocks the plurality of second driving rotators with each other. A movement distance per unit rotation angle of each of the plurality of first driving rotators in the displacement member may be different from a movement distance per unit rotation angle of each of the plurality of second driving rotators in the displacement member. According to the aforementioned configuration, the first driving rotators and the second driving rotators are different from each other in speed of moving the displacement member. Therefore, a release speed of the stent from the sheath can be relatively easily controlled by rotating the first driving rotators or the second driving rotators in accordance with an intended speed of releasing the stent.

In the stent delivery system, the first interlocking portion may have a plurality of first rotative portions which are coaxially and respectively provided in the plurality of first driving rotators, and at least one first transmission member which comes into contact with the plurality of first rotative portions so as to be able to transmit power thereto. The second interlocking portion may have a plurality of second rotative portions, which are coaxially and respectively provided in the plurality of second driving rotators, and at least one second transmission member, which comes into contact with the plurality of second rotative portions so as to be able to transmit power thereto. According to the aforementioned configuration, the plurality of first driving rotators can be reliably interlocked with each other in simple structure, and the plurality of second driving rotators can be reliably interlocked with each other in simple structure.

In the stent delivery system, the displacement member may have first and second driven portions on sides opposite to each other. The plurality of first driving rotators may abut on the first driven portion and drive the displacement member. The plurality of second driving rotators may abut on the second driven portion and drive the displacement member. According to the aforementioned configuration, since the first driving rotators and the second driving rotators are arranged on sides opposite to each other while interposing a movement path of the displacement member therebetween, the first driving rotators and the second driving rotators, which are respectively provided to be plural in number can be efficiently arranged inside the grip.

In the stent delivery system, one of the plurality of first driving rotators may be provided in a first rotative operation portion, which is rotatably supported by the grip. One of the plurality of second driving rotators may be provided in a second rotative operation portion, which is rotatably supported by the grip. The first rotative operation portion and the second rotative operation portion may be exposed on outer side surfaces of the grip on sides opposite to each other. According to the aforementioned configuration, since the first rotative operation portion and the second rotative operation portion are exposed from the grip on sides different from each other, it is relatively easy for a user to discriminate between the first rotative operation portion and the second rotative operation portion, which are thereby suitably and easily used.

In the stent delivery system, a plurality of the stents may be arranged side by side along the axial direction of the inner member. The number of the driving rotators may be the same as the number of the stents. Every time the driving rotators rotate in order from the driving rotator on a distal side, the stents may be released from the sheath in order from the stent on the distal side. According to the aforementioned configuration, when the plurality of stents are provided along the axial direction, the stents are released from the sheath in order from the stent on the distal side by rotating the driving rotators in order from the driving rotator on the distal side. In accordance with an exemplary embodiment, since each rotator corresponds to the arrangement of each stent, only the stent, which is intended to be released, is reliably released, through simple operation at each stage of releasing the plurality of stents.

In the stent delivery system, at least one of the driving rotators may be different from the remaining driving rotators in a movement distance per unit rotation angle of each of the driving rotators in the displacement member. According to the aforementioned configuration, a movement speed at the time of moving the displacement member is not uniform. The movement speed varies depending on the driving rotator. Therefore, due to the arrangement of the driving rotators, the release speed at each stage of releasing the stent from the sheath can be controlled. Thus, a procedure can be appropriately and efficiently conducted.

In the stent delivery system, the plurality of driving rotators may include a plurality of first driving rotators and a plurality of second driving rotators. At least one of the first driving rotators and at least one of the second driving rotators may be able to drive the displacement member at all times within a movable range of the displacement member. A movement distance per unit rotation angle of each of the plurality of first driving rotators in the displacement member may be different from a movement distance per unit rotation angle of each of the plurality of second driving rotators in the displacement member. According to the aforementioned configuration, the first driving rotators and the second driving rotators are different from each other in speed of moving the displacement member. Therefore, a release speed of the stent from the sheath can be relatively easily controlled by rotating the first driving rotators or the second driving rotators in accordance with an intended speed of releasing the stent.

In the stent delivery system, the displacement member may have first and second driven portions on sides opposite to each other. The plurality of first driving rotators may abut on the first driven portion and drive the displacement member. The plurality of second driving rotators may abut on the second driven portion and drive the displacement member. According to the aforementioned configuration, since the first driving rotators and the second driving rotators are arranged on sides opposite to each other while having a movement path of the displacement member as a reference, the first driving rotators and the second driving rotators, which are respectively provided to be plural in number can be efficiently arranged inside the grip.

In the stent delivery system, the first driving rotators may be respectively provided in a plurality of first rotative operation portions, which are rotatably supported by the grip. The second driving rotators may be respectively provided in a plurality of second rotative operation portions, which are rotatably supported by the grip. The plurality of first rotative operation portions and the plurality of second rotative operation portions may be respectively exposed on outer side surfaces of the grip on sides opposite to each other. According to the aforementioned configuration, since the first rotative operation portion and the second rotative operation portion are exposed from the grip on sides different from each other, it can be relatively easy for a user to discriminate between the first rotative operation portion and the second rotative operation portion, which are thereby relatively suitably and easily used.

In the stent delivery system, a movement distance per unit rotation angle of the driving rotator provided on the farthest proximal side in the displacement member may be greater than a movement distance per unit rotation angle of the driving rotator provided on the farthest distal side in the displacement member. According to the aforementioned configuration, the stent can be easily positioned at the initial stage of release by releasing the stent slowly, and a procedure can finish early at the end stage of release by releasing the stent relatively quickly.

In the stent delivery system, the driving rotator provided on the farthest distal side may be provided in a first rotative operation portion, which is rotatably supported by the grip. The driving rotator provided on the farthest proximal side may be provided in a second rotative operation portion, which is rotatably supported by the grip. The first rotative operation portion and the second rotative operation portion may be exposed on outer side surfaces of the grip on sides opposite to each other. According to the aforementioned configuration, since the first rotative operation portion and the second rotative operation portion are exposed from the grip on sides different from each other, it is relatively easy for a user to discriminate between the first rotative operation portion and the second rotative operation portion, which are thereby suitably and easily used.

In the stent delivery system, a position of the displacement member may be visually recognizable from the outside of the grip. According to the aforementioned configuration, since the position of the displacement member can be viewed during a procedure, the timing of changing the driving rotator to be rotated can be known, and a procedure of releasing the stent through efficient operation can be performed.

According to the stent delivery system of the present disclosure, a stent can be released and indwell in a living body lumen without elongating the overall length of a grip even when a stent having the quite long overall length or a plurality of stents are applied.

BRIEF DESCRIPTION OF THE DRAWINGS

FIG. 4A is a first diagram explaining an operation of the stent delivery system illustrated in FIG. 1.

FIG. 4B is a second diagram explaining an operation of the stent delivery system illustrated in FIG. 1.

FIG. 4C is a third diagram explaining an operation of the stent delivery system illustrated in FIG. 1.

FIG. 11 is a perspective view of the movement mechanism in the stent delivery system illustrated in FIG. 9.

FIG. 12A is a first diagram explaining an operation of the stent delivery system illustrated in FIG. 9.

FIG. 12B is a second diagram explaining an operation of the stent delivery system illustrated in FIG. 9.

FIG. 12C is a third diagram explaining an operation of the stent delivery system illustrated in FIG. 9.

FIG. 13A is a first diagram explaining an operation of the stent delivery system in the modification example.

FIG. 13B is a second diagram explaining an operation of the stent delivery system in the modification example.

FIG. 13C is a third diagram explaining an operation of the stent delivery system in the modification example.

FIG. 15 is a partially omitted side view of a stent delivery system according to a seventh embodiment of the present disclosure.

DETAILED DESCRIPTION

Hereinafter, suitable embodiments will be exemplified regarding a stent delivery system according to the present disclosure and description will be given with reference to the accompanying drawings.

Figure 1:
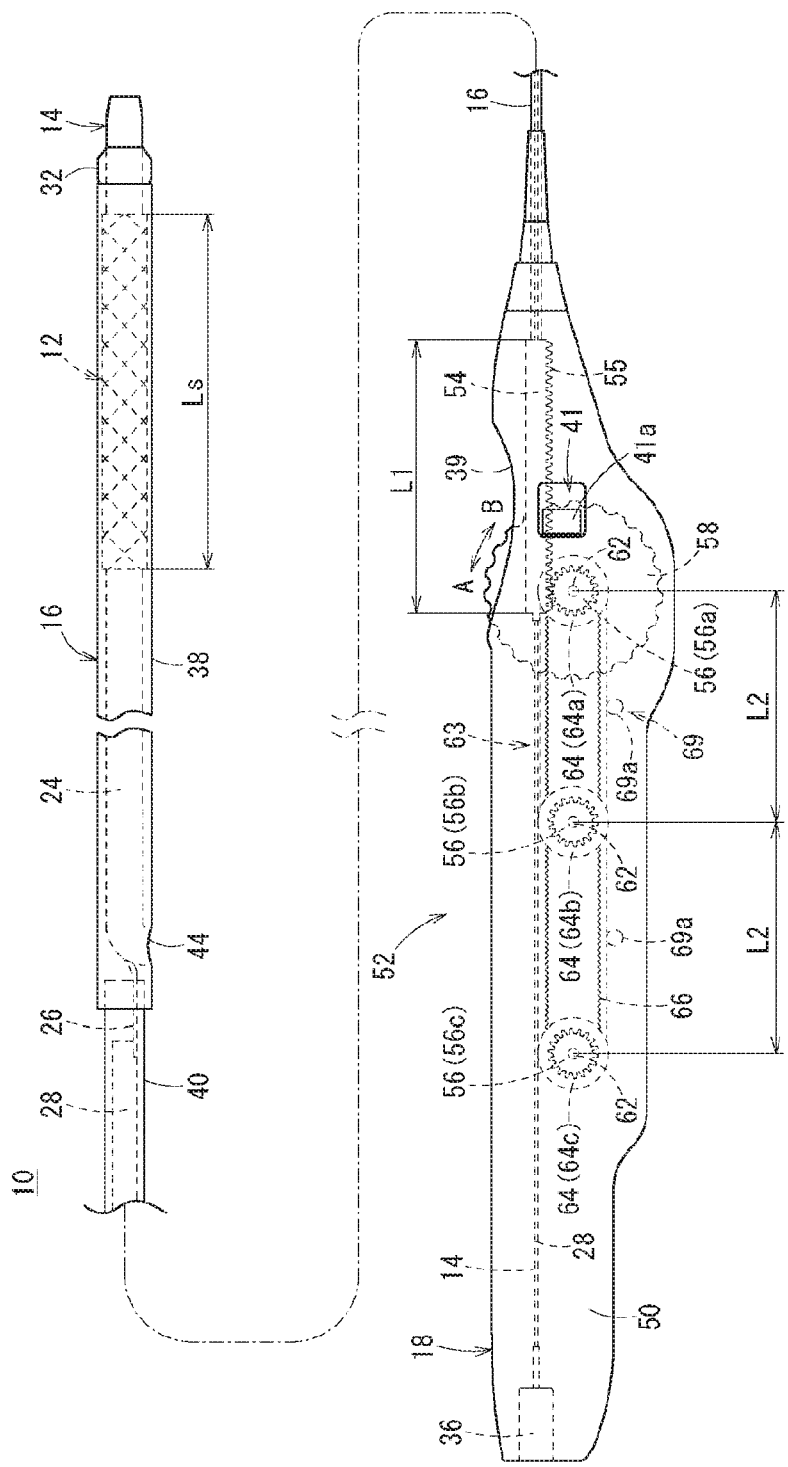
FIG. 1 is a partially omitted side view of a stent delivery system according to a first embodiment of the present disclosure.
Figure 6:
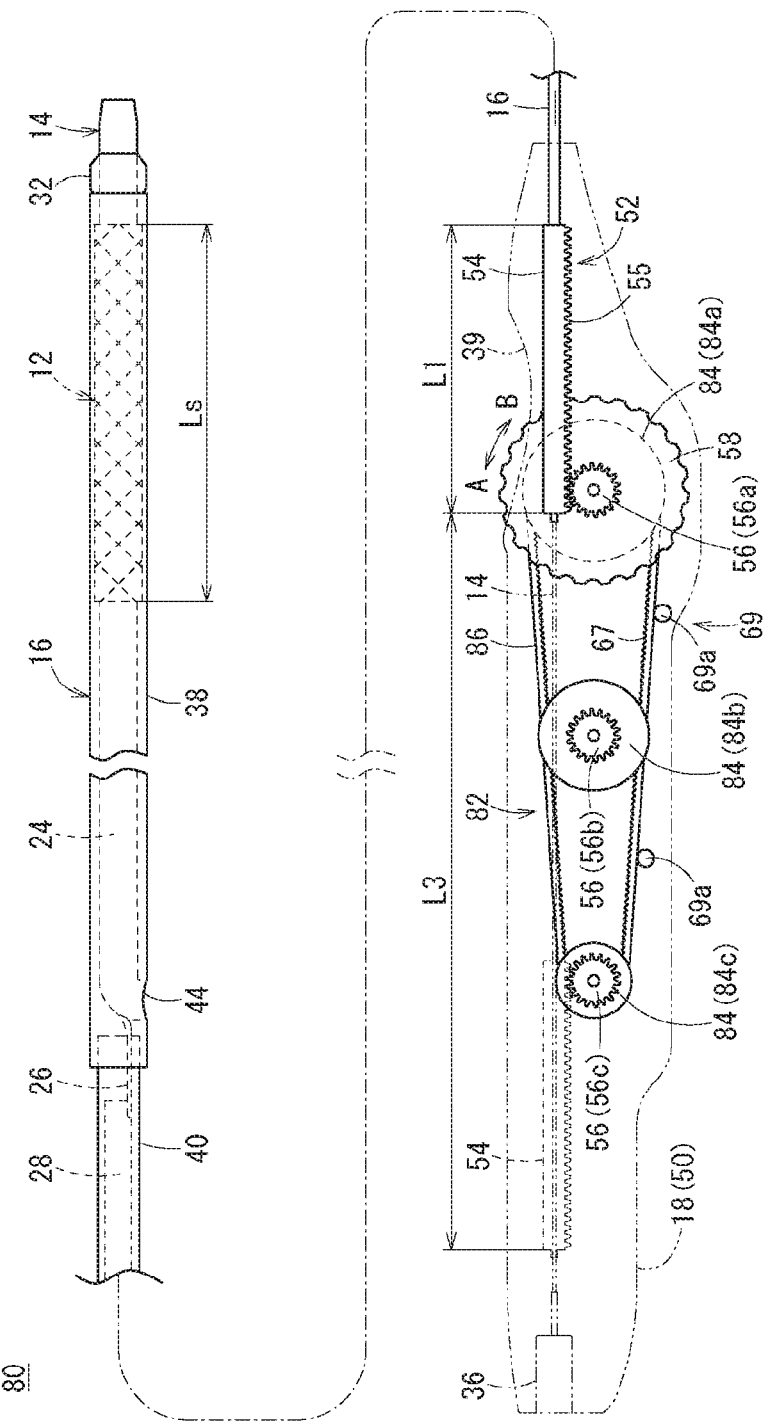
FIG. 6 is a partially omitted side view of a stent delivery system according to a second embodiment of the present disclosure.
Figure 7:
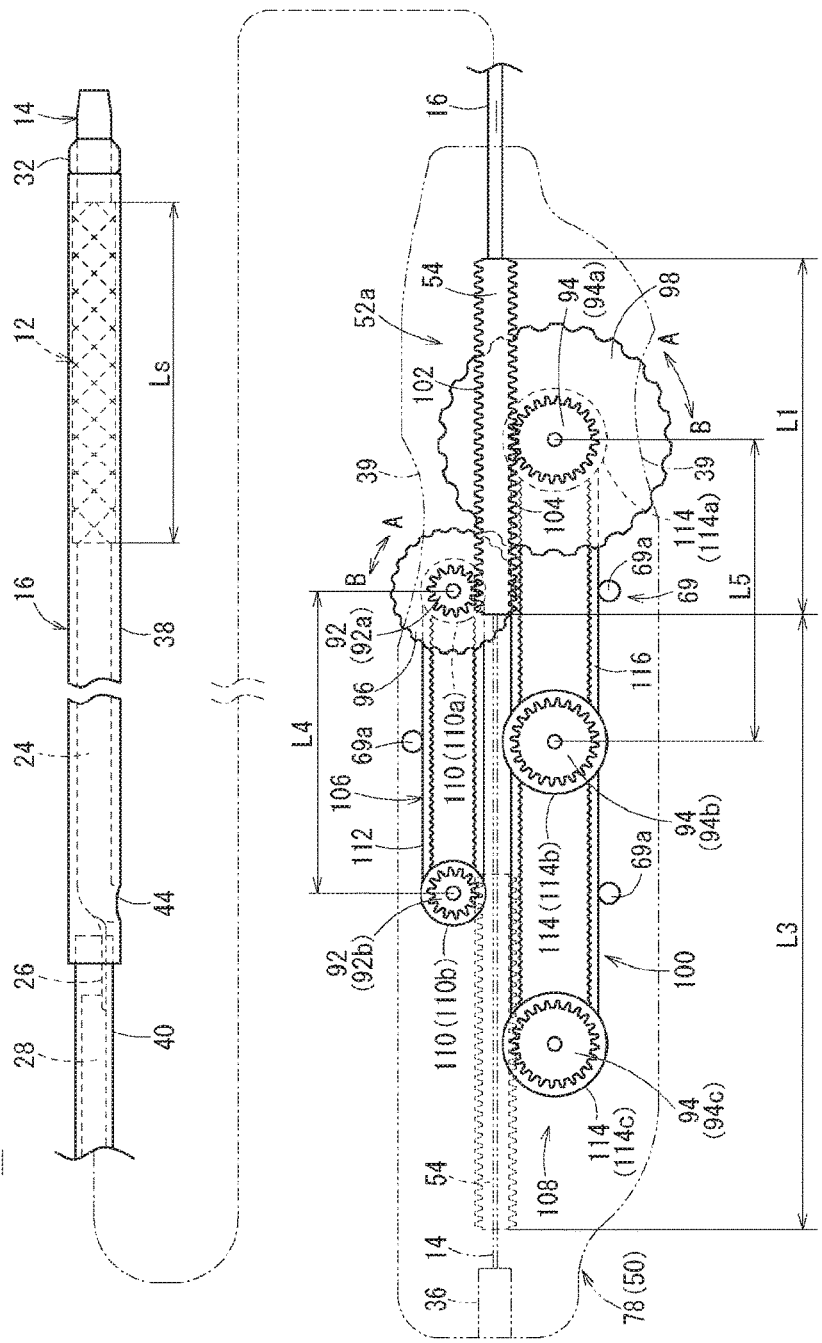
FIG. 7 is a partially omitted side view of a stent delivery system according to a third embodiment of the present disclosure.
Figure 8:
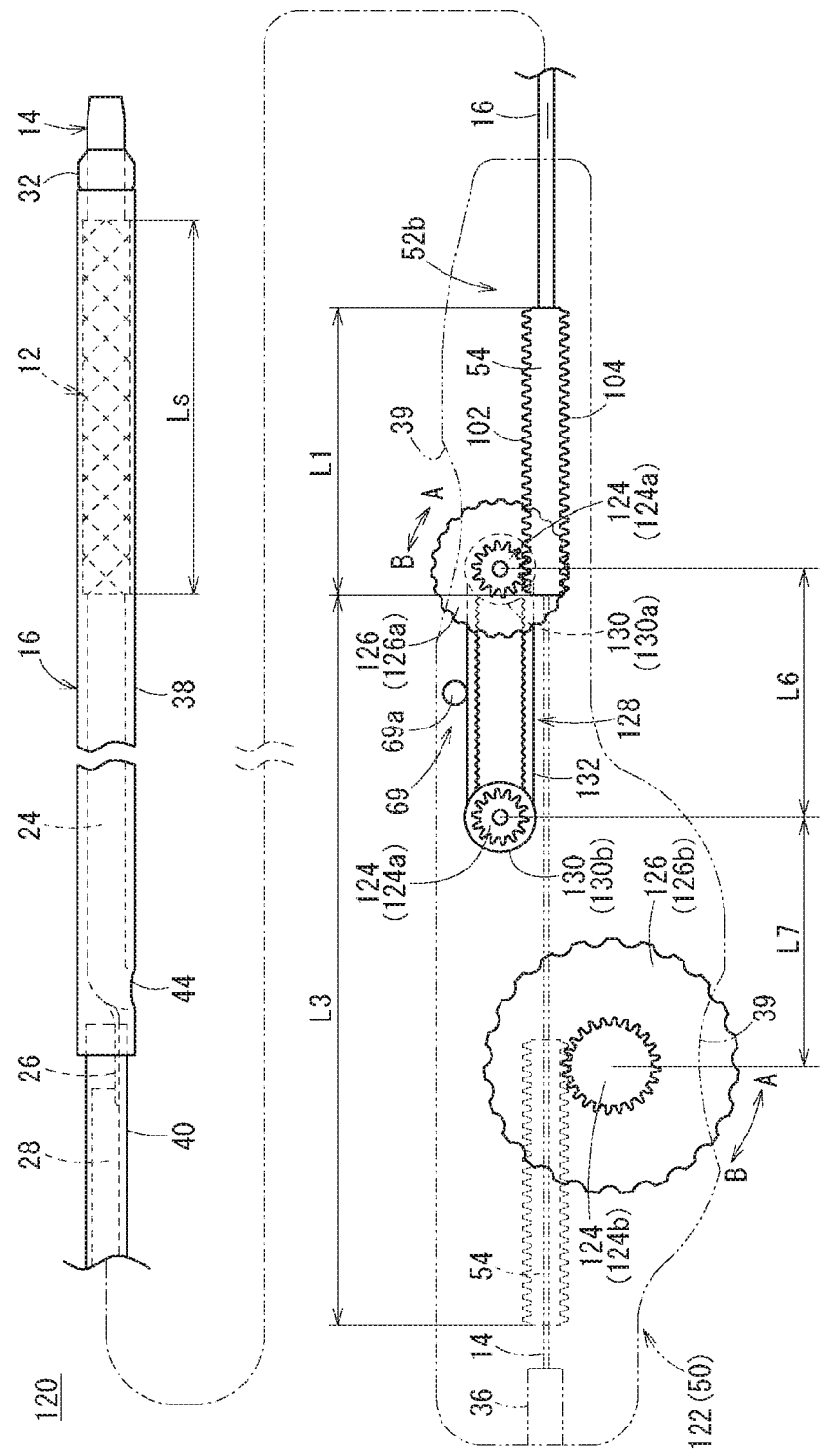
FIG. 8 is a partially omitted side view of a stent delivery system according to a fourth embodiment of the present disclosure.

FIG. 1 is a partially omitted side view of a stent delivery system 10 according to a first embodiment of the present disclosure. In FIG. 1, for convenience of illustration, illustration of an intermediate portion of the stent delivery system 10 in an axial direction is omitted, and a distal side (a stent 12 side) of the stent delivery system 10 is depicted to be greater than a proximal side (a grip 18 side) thereof. Note that, the aforementioned point is similarly applied to FIGS. 6 to 8 illustrating second to fourth embodiments.

In accordance with an exemplary embodiment, the stent delivery system 10 is a medical device for delivering a stent 12 to a desired position inside a living body lumen such as a blood vessel, the bile duct, the trachea, the esophagus, the urethra, and the like and making the stent to indwell therein. The stent delivery system 10 is provided with an inner tube 14 (an inner member), an outer tube 16 (a sheath) which is arranged outside the inner tube 14, the self-expandable stent 12 which is arranged between the inner tube 14 and the outer tube 16, and a grip 18 which is provided on the proximal end side of the outer tube 16.

Regarding the stent delivery system 10 in FIG. 1, a side or a direction provided with the grip 18 is referred to as "the proximal side" or "the proximal direction", and the opposite side or the opposite direction thereof is referred to as "the distal side" or "the distal direction". The same is applied to those in other diagrams.

Figure 2:
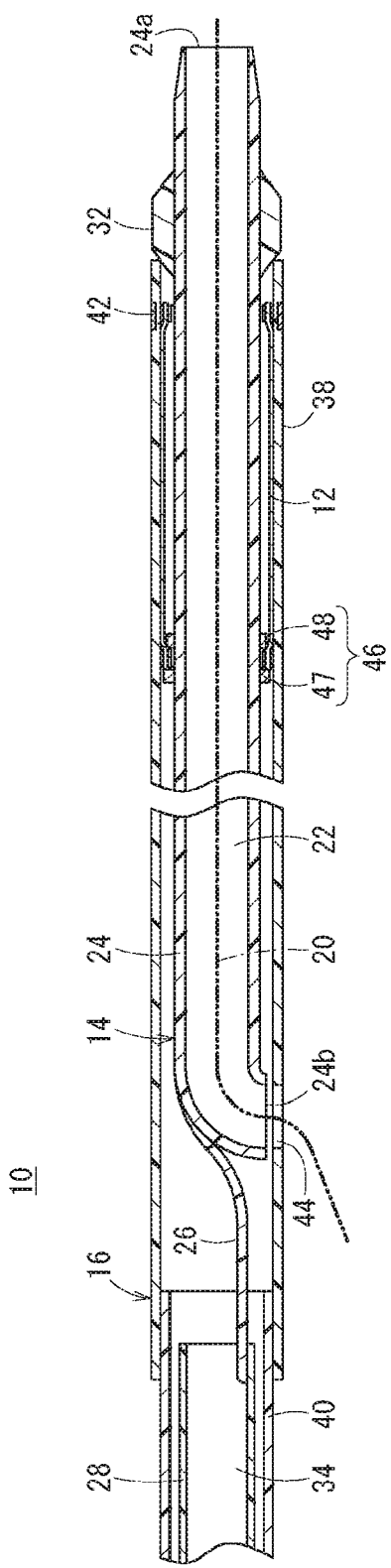
FIG. 2 is a partially omitted longitudinal sectional view of an inner tube and an outer tube in the stent delivery system illustrated in FIG. 1.

As illustrated in FIG. 2, the inner tube 14 has an inner distal tube 24 in which a guide wire lumen 22 for allowing a guide wire 20 to be inserted therethrough is formed, and an inner proximal tube 28 which is connected to the proximal end of the inner distal tube 24 via a connection member 26. The distal end of the inner tube 14, that is, the distal end of the inner distal tube 24 protrudes toward the distal side beyond the distal end of the outer tube 16.

A distal end opening 24a which is open in the distal direction is formed at the distal end of the inner distal tube 24. The proximal end of the inner distal tube 24 is curved radially to the outside of the inner distal tube 24, and a proximal end opening 24b which is open radially outward is formed at the proximal end thereof. In the initial state (the state in FIG. 2) of the stent delivery system 10, the proximal end opening 24b communicates with a guide wire leading-out hole 44 described below. Note that, for example, the guide wire 20 is applied in order to lead the stent delivery system 10 to a lesion inside a living body lumen.

A stopper portion 32 which protrudes radially outward and prevents the outer tube 16 from moving in the distal direction is formed in a distal portion of the inner distal tube 24. Since the stopper portion 32 helps prevent the outer tube 16 from moving in the distal direction, the outer tube 16 is prevented from protruding in the distal direction beyond the distal end of the inner tube 14.

The connection member 26 is connected to the proximal end of the inner distal tube 24 and the distal end of the inner proximal tube 28. The inner proximal end tube 28 has a lumen 34, which penetrates from the distal end to the proximal end thereof. As illustrated in FIG. 1, the inner proximal tube 28 protrudes in the proximal direction beyond the proximal end of the outer tube 16 in the grip 18 and linearly extends in the grip 18.

A proximal end of the inner proximal tube 28 is connected to a connector 36 which is provided in a proximal portion of the grip 18. A liquid injector for supplying liquid such as a physiological salt solution and the like to the stent delivery system 10 can be connected to the connector 36. The proximal end of the inner proximal tube 28 and the connector 36 are fixed. Consequently, the inner tube 14 is fixed so as not to move in the axial direction with respect to the grip 18.

The aforementioned inner tube 14 can be configured to be formed with a resin material, a metal material, or the like. Note that, it can be preferable that the inner distal tube 24 is configured to be formed with a material having higher flexibility than that of the inner proximal tube 28.

The outer tube 16 is provided so as to be movable in the axial direction with respect to the inner tube 14 and the grip 18. In the present illustrated example, the outer tube 16 has an outer distal tube 38 and an outer proximal tube 40, which is connected to the proximal end of the outer distal tube 38. The inner distal tube 24 of the inner tube 14 is arranged inside the outer distal tube 38.

The inner proximal tube 28 of the inner tube 14 is arranged inside the outer proximal tube 40. The proximal end of the outer tube 16, that is, the proximal end of the outer proximal tube 40 is inserted into the grip 18.

The distal end of the outer distal tube 38 functions as a release port of the stent 12 when the stent 12 indwells in a lesion inside a living body lumen and also functions as a containing port when recovering (containing again) the stent 12 which has been released partway.

The guide wire leading-out hole 44 through which the inside and outside of the outer distal tube 38 communicate with each other is formed in the vicinity of the proximal end of the outer distal tube 38. As illustrated in FIG. 2, in the initial state of the stent delivery system 10, the proximal end opening 24b of the inner distal tube 24 and the guide wire leading-out hole 44 communicate with each other. Accordingly, the guide wire 20 can be inserted into the guide wire lumen 22 via the distal end opening 24a of the inner distal tube 24. Furthermore, the guide wire 20 can be led out of the outer tube 16 via the proximal end opening 24b and the guide wire leading-out hole 44.

As illustrated in FIG. 2, it can be preferable that a contrast marker 42 formed with an X-ray (radiation) opaque material is provided on the outer circumferential surface of the distal portion of the outer distal tube 38.

The stent 12 is formed to have a substantially cylindrical shape and to be self-expandable. For example, in the initial state of the stent delivery system 10, the stent 12 can be arranged between the inner tube 14 and the outer tube 16 in a contracted state. In accordance with an exemplary embodiment, the stent 12 is included in the outer tube 16 in a state of being prevented from expanding by the outer tube 16 and being compressed in a radially inward direction. In addition, in accordance with a movement of the outer tube 16 in the proximal direction with respect to the inner tube 14, the stent 12 can be released from the outer tube 16. Therefore, the stent 12 expands in a radially outward direction due to its own elastic restoring force. A length Ls of the stent 12 varies depending on a treatment target site. However, the length Ls ranges approximately from, for example, 10 mm to 300 mm, and it can be preferable that the length Ls ranges approximately from, for example, 40 mm to 250 mm.

In accordance with an exemplary embodiment, as a configuration of the stent 12, for example, a mesh-like configuration in which multiple side holes are provided, a configuration in which multiple circular ring bodies are connected in the axial direction, a configuration in which multiple ring bodies extending in a circumferential direction in a zigzag manner are connected in the axial direction, and the like can be exemplified. As a configurational material of the stent 12, for example, a super-elastic alloy such as a Ni—Ti alloy and the like is suitable. In accordance with an exemplary embodiment, it can be preferable that a contrast marker formed with an X-ray opaque material, for example, is provided at the distal end and the proximal end of the stent 12.

As illustrated in FIG. 2, a stent holding mechanism 46 which helps prevent the stent 12 from moving in the axial direction is provided in the outer circumferential portion of the inner tube 14 (specifically, the inner distal tube 24). The stent holding mechanism 46 has a rearward movement preventing stopper 47, which helps prevent the stent 12 from moving in the proximal direction and a forward movement preventing stopper 48 which helps prevent the stent 12 from moving in the distal direction.

In accordance with an exemplary embodiment, the rearward movement preventing stopper 47 helps prevent the stent 12 from moving rearward by engaging with the proximal end of the stent 12 having a decreased diameter when the outer tube 16 is moved in the proximal direction with respect to the inner tube 14 in order to release the stent 12. The forward movement preventing stopper 48 helps prevent the stent 12 from moving forward by engaging with the proximal end of the stent 12 having a decreased diameter when the outer tube 16 is moved in the distal direction with respect to the inner tube 14 in order to cause the stent 12 which has been released partway to be contained again inside the outer tube 16.

In FIG. 1, the grip 18 configured to form the proximal portion of the stent delivery system 10 is a portion which functions as a handle so that a user grips and operates the handle with one's hand. The grip 18 has a hollow housing 50 and is configured to be slightly elongated in the axial direction (a front-rear direction) of the stent delivery system 10. A movement mechanism 52 for moving the outer tube 16 in the axial direction with respect to the inner tube 14 is provided inside the housing 50.

Figure 3:
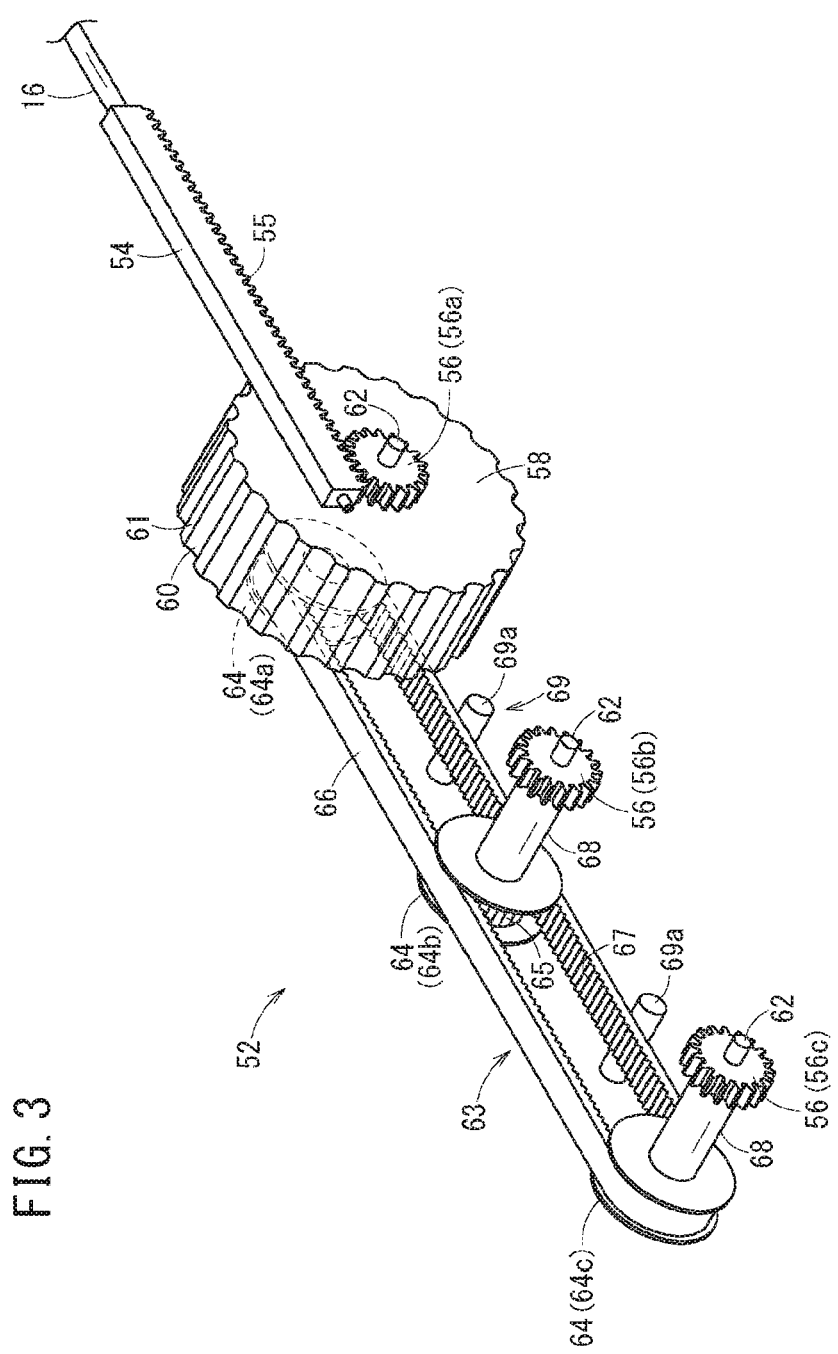
FIG. 3 is a perspective view of a movement mechanism in the stent delivery system illustrated in FIG. 1.

As illustrated in FIGS. 1 and 3, the movement mechanism 52 has a rack member 54 (a displacement member) which is connected to the outer tube 16, which is movable in the axial direction of the stent delivery system 10, and which extends in the axial direction; a plurality of (three in the illustrated example) pinions 56 (driving rotators) which are arranged at intervals from each other in an extension direction of the rack member 54 and move the rack member 54 in the extension direction in accordance with rotations thereof; an interlocking mechanism 63 which interlocks the plurality of pinions 56 with each other; and an operation wheel 58 (a rotative operation portion) which rotates the plurality of pinions 56 via the interlocking mechanism 63. In accordance with an exemplary embodiment, for example, two pinions 56 may be provided as well as four or more thereof.

In accordance with an exemplary embodiment, the rack member 54 is supported by a guide portion (not illustrated), which is provided inside the housing 50, in a slidable manner in the axial direction (the front-rear direction of the grip 18) of the stent delivery system 10. Since the rack member 54 is fixed to the proximal end portion of the outer tube 16, the outer tube 16 also moves while being interlocked with the rack member 54. The rack member 54 (the bottom surface of the rack member 54 in the illustrated example) is provided with a rack 55 which can include a plurality of tooth portions along the axial direction of the rack member 54.

In accordance with an exemplary embodiment, as position recognizing means for the rack member 54, the housing 50 may be configured to be formed with a transparent material partially or in its entirety. Otherwise, the housing 50 may be partially provided with an opening for exposing the rack member 54 so that a position of the rack member 54 inside the housing 50 is visually recognizable from the outside of the housing 50. Otherwise, as another configuration of the position recognizing means, the rack member 54 may be configured to be provided with a projection so that the projection protrudes from the housing 50 via a slit provided in the housing 50, and thus, the position of the rack member 54 can be recognized based on a position of the projection.

Each of the pinions 56 (56a to 56c) can mesh with the rack 55 of the rack member 54. Rotary axis centers of the three pinions 56 are parallel to each other. In addition, the rotary axis centers of the three pinions 56 extend on a straight line, which is parallel to the rack member 54 in a movable direction (the extension direction).

In FIG. 1, both center-to-center distances L2 of two pairs of adjacent pinions 56 in the three pinions 56a to 56c are equal to each other. A length L1 (the length of the rack 55) of the rack member 54 is greater than the center-to-center distance L2 between the pinions 56. Therefore, the rack 55 can mesh with at least two adjacent pinions 56. All the numbers of teeth and modules are the same in the three pinions 56a to 56c. In accordance with an exemplary embodiment, a module (m) is a value, which is obtained by dividing a pitch circle diameter (d) by the number of teeth (z). In accordance with an exemplary embodiment, the center-to-center distances L2 of the two pairs of adjacent pinions 56 in the three pinions 56a to 56c may be different from each other.

A pinion 56a on the farthest distal side is provided in a radially central portion of the operation wheel 58. As illustrated in FIG. 3, the outer circumferential portion of the operation wheel 58 can be formed to have an antislip shape in which grooves 60 and protrusions 61 are alternately arranged in the circumferential direction. The operation wheel 58 has a shaft portion 62, which protrudes in the axial direction thereof. The shaft portion 62 is supported by a bearing portion which is provided in the housing 50 on the inner side. Therefore, the operation wheel 58 is rotatably supported by the housing 50. Note that, each of remaining pinions 56b and 56c also has the shaft portion 62 which protrudes in the axial direction thereof, and each of the shaft portions 62 is supported by the bearing portion which is provided in the housing 50 on the inner side.

In FIG. 1, the housing 50 is provided with an opening portion 39 for partially exposing the operation wheel 58. A user can rotatively operate the operation wheel 58 by contact an exposed portion of the operation wheel 58 through the opening portion 39.

As illustrated in FIGS. 1 and 3, the interlocking mechanism 63 has a plurality of pulleys 64 (rotative portions), which are coaxially and respectively provided in the plurality of pinions 56, and a belt 66 (a transmission member) which comes into contact with the plurality of pulleys 64 so as to be able to transmit power thereto. In the illustrated example, a pulley 64a on the farthest distal side is provided on a side opposite to the pinion 56a in the operation wheel 58. Accordingly, the operation wheel 58, the pinion 56a, and the pulley 64a are coaxially arranged so as to integrally rotate.

Remaining pulleys 64b and 64c are respectively connected to the remaining pinions 56b and 56c via a connection shaft 68. Accordingly, the pinion 56b and the pulley 64b which are provided in the middle portion rotate integrally. In addition, the pinion 56c and the pulley 64c which are provided on the farthest proximal side integrally rotate.

In the present embodiment, all of the diameters (the pitch circle diameter) of the three pulleys 64 are equal to each other. Accordingly, when the three pulleys 64 rotate while being interlocked with each other by the belt 66, all of the rotational speeds of the three pulleys 64 are equal.

In accordance with an exemplary embodiment, the belt 66 is a flexible endless member (an annular member) and can be configured to be formed with a resin material, for example. In the present illustrated example, the belt 66 is wound around the pulley 64a on the farthest distal side and the pulley 64c on the farthest proximal side and comes into contact with the outer circumferential portions (an upper portion and a lower portion) of the pulley 64b which is provided in the middle portion. Note that, it can be preferable that the belt 66 comes into contact with at least a portion of the pulley 64b which is provided in the middle portion. For example, the belt 66 may come into contact with only the upper portion or only the lower portion of the pulley 64b.

In the present illustrated example, each of the pulleys 64 is a toothed pulley in which a plurality of teeth 65 are formed in the outer circumferential portion along the circumferential direction. The belt 66 is a toothed belt which meshes with each of the pulleys 64 and in which a plurality of teeth 67 are formed in the inner circumferential portion. Therefore, the three pulleys 64 can be reliably interlocked with each other without causing a slip between each of the pulleys 64 and the belt 66. Note that, when friction force can be sufficiently ensured due to contact between the outer circumferential surface of each of the pulleys 64 and the inner circumferential surface of the belt 66, each pulley 64 and the belt 66 may be a flat pulley and a flat belt having no tooth formed therein. In accordance with an exemplary embodiment, each pulley 64 and the belt 66 may also be a V-pulley and a V-belt.

Due to the aforementioned configuration of the interlocking mechanism 63, when the operation wheel 58 is rotatively operated, rotations of the pulley 64a on the farthest distal side are transmitted to the remaining pulleys 64b and 64c via the belt 66. Accordingly, the plurality of pinions 56 can rotate while being interlocked with each other and the rack member 54 can thereby move forward or rearward by only rotatively operating one operation wheel 58. Note that, in the present illustrated example, the pinion 56a on the farthest distal side is provided in the operation wheel 58. However, any one of the remaining pinions 56b and 56c may be provided in the operation wheel 58.

As illustrated in FIGS. 1 and 3, in accordance with an exemplary, it can be preferable that the interlocking mechanism 63 is provided with a tension applying mechanism 69 for applying suitable tension to the belt 66. In the illustrated example, the tension applying mechanism 69 has a plurality of (two) tension pins 69a, which come into contact with the outer circumferential surface of the belt 66. The tension pins 69a are fixed to the inside of the housing 50 (refer to FIG. 1).

The tension pin 69a on one side comes into contact with a bridge portion of the belt 66 between the pulley 64b provided in the middle portion and the pulley 64a provided on the farthest distal side. The tension pin 69a on other side comes into contact with a bridge portion of the belt 66 between the pulley 64b provided in the middle portion and the pulley 64c provided on the farthest proximal side. Due to the tension pins 69a, the belt 66 can be reliably wound around each of the pulleys 64a and 64c on the farthest distal side and the farthest proximal side. In addition, since the belt 66 is adjusted so as to come into contact with the pulley 64b in the middle portion by the tension pins 69a, the pulley 64b and the belt 66 reliably mesh with each other.

Note that, in accordance with an exemplary embodiment, one tension pin 69a may be provided. In addition, as an alternative configuration of the tension applying mechanism 69, one or a plurality of tension rollers which come into contact with the outer circumferential surface of the belt 66 may be provided in place of the tension pins 69a.

The grip 18 is provided with a lock mechanism 41 which can help prevent a movement operation of the rack member 54 by preventing a rotational operation of the operation wheel 58. The lock mechanism 41 has a slide member 41a which is provided on a side surface of the housing 50 in a slidable manner. The slide member 41a can move between a locked position where a rotational operation of the operation wheel 58 are prevented and an unlocked position where a rotational operation of the operation wheel 58 is allowed. The slide member 41a is provided with a lock pin (not illustrated) which protrudes toward the inside of the housing 50.

Meanwhile, in accordance with an exemplary embodiment, the operation wheel 58 is provided with an engagement portion (not illustrated) (for example, a groove portion) which can engage with the lock pin. When the slide member 41a is located at the locked position, the lock pin engages with the engagement portion, thereby preventing a rotational operation of the operation wheel 58. Meanwhile, when the slide member 41a is located at the unlocked position, the lock pin is separated from the engagement portion, thereby allowing a rotational operation of the operation wheel 58.

The stent delivery system 10 according to the present embodiment generally has the aforementioned configuration. Hereinafter, operations and effects thereof will be described.

In a procedure of treating a lesion (for example, a stenosed site), which has occurred inside a living body lumen (for example, inside a blood vessel) by applying the stent delivery system 10, prior to the stent delivery system 10 being inserted into the living body lumen, the guide wire 20 (refer to FIG. 2) is inserted into the living body lumen. Then, the distal end of the guide wire 20 is in a state of having reached the lesion inside a living body lumen.

At the aforementioned state, priming for filling the insides of the inner tube 14 and the outer tube 16 in the stent delivery system 10 outside a living body with predetermined liquid (for example, a physiological salt solution or the like) is performed. In priming, first, an operator connects a liquid injection device (not illustrated) to the connector 36 which is provided in the proximal end of the grip 18 and injects the liquid into the connector 36 through the liquid injection device. Consequently, the liquid flows toward the distal sides of the inner tube 14 and the outer tube 16, thereby flowing out from each of the distal ends of the inner tube 14 and the outer tube 16. In this manner, priming performed for the insides of the inner tube 14 and the outer tube 16 outside the living body finishes.

Subsequently, as illustrated in FIG. 2, the proximal end of the guide wire 20 exposed to the outside of the living body is inserted through the guide wire lumen 22 from the distal end of the inner tube 14, thereby being led out of the outer tube 16 through the guide wire leading-out hole 44. Then, the inner tube 14 and the outer tube 16 are caused to move forward to the inside of the living body lumen along the guide wire 20.

Then, the distal end of the outer tube 16 is confirmed for arrival at the lesion by using the contrast marker 42. Thereafter, the slide member 41a provided in the grip 18 moves to the distal side, thereby cancelling the state of preventing rotations of the operation wheel 58. At this moment, as illustrated in FIG. 4A, the rack member 54 is positioned on the farthest distal side within a movable range thereof. In FIG. 4A, a position of the rack member 54 when the stent 12 is in a state of being completely released from the distal end of the outer tube 16 is indicated by the dotted line. A reference number L3 indicates a necessary movement distance in the rack member 54 for completely releasing the stent 12 from the distal end of the outer tube 16.

When the state of preventing rotations of the operation wheel 58 is cancelled, the operation wheel 58 is rotated in a predetermined direction (an arrow A direction) by contacting the portion of the operation wheel 58 exposed from the housing 50 via the opening portion 39. Consequently, the rack member 54 moves to the proximal side inside the housing 50 in accordance with rotations of the pinion 56a which is provided in the operation wheel 58. Consequently, the outer tube 16, which is connected to the rack member 54 also moves in the proximal direction of the grip 18.

As a result thereof, in accordance with a movement of the outer tube 16 in the proximal direction with respect to the inner tube 14, the stent 12 which is accommodated inside the outer tube 16 (refer to FIG. 1) begins to be gradually exposed from the distal side and begins to expand radially outward at the same time. In accordance with an exemplary embodiment, for example, the stent 12 is released in accordance with a movement of the outer tube 16 in the proximal direction. Note that, when it is intended to adjust a position of the stent 12 inside a living body lumen at a stage where the stent 12 is released partway, the operation wheel 58 may be rotatively operated in the reverse direction (an arrow B direction). In this manner, the outer tube 16 moves in the distal direction so that the stent 12 can be contained again inside the outer tube 16.

When the rack member 54 moves in the proximal direction in accordance with a rotative operation of the operation wheel 58, as illustrated in FIG. 4B, the rack 55 of the rack member 54 eventually meshes with the pinion 56b which is provided right next thereto on the proximal side. In this case, the stent 12 is in a state of being released partway (approximately one third of the overall length).

Since the pulley 64b provided in the middle portion is interlocked with the pulley 64a on the farthest distal side via the belt 66, the pinion 56b provided in the middle portion also rotates in accordance with a rotative operation with respect to the operation wheel 58. Accordingly, when the operation wheel 58 is rotatively operated further in the arrow A direction, even though the meshed state between the rack member 54 and the pinion 56a on the farthest distal side is removed, the rack member 54 is driven by the pinion 56b provided in the middle portion, thereby moving in the proximal direction. As the pinion 56b is driven in the aforementioned manner, the outer tube 16 is moved in the proximal direction and the stent 12 is released further.

When the rack member 54 moves in the proximal direction in accordance with a rotative operation of the operation wheel 58, as illustrated in FIG. 4C, the rack 55 of the rack member 54 eventually meshes with the pinion 56c which is provided next but one to the proximal side. In this case, the stent 12 is in a state of being released partway (approximately two third of the overall length).

Since the pulley 64c of the farthest proximal side is interlocked with the pulley 64a on the farthest distal side via the belt 66, the pinion 56c on the farthest proximal side also rotates in accordance with a rotative operation with respect to the operation wheel 58 provided with the pulley 64a. Accordingly, when the operation wheel 58 is rotatively operated further in the arrow A direction, even though the meshed state between the rack member 54 and the pinion 56b provided in the middle portion is removed, the rack member 54 is driven by the pinion 56c on the farthest proximal side, thereby moving in the proximal direction. As the pinion 56c is driven in the aforementioned manner, the outer tube 16 is moved in the proximal direction and the stent 12 is released further.

Then, the stent 12 is in a state of being completely exposed from the outer tube 16 (a state where the overall length of the stent 12 is released). In this manner, the stent 12 indwells in a lesion in a cylindrically expanded state.

Thereafter, the inner tube 14 and the outer tube 16 configuring the stent delivery system 10 are pulled to the proximal side so that the inner tube 14 and the outer tube 16 are evulsed out of a living body while leaving only the stent 12 inside a biological lumen.

Note that, only one stent 12 is provided in the stent delivery system 10 illustrated in FIG. 1. However, the present disclosure is not limited to this configuration and may be applied with a configuration in which plurality of stents 12 are arranged side by side in the axial direction. For example, in a case of the stent delivery system 10 provided with two stents 12 (stents shorter than the stent 12 illustrated in FIG. 1) which are arranged side by side in the axial direction, the stent delivery system 10 operates as follows.

For example, in accordance with movements of the rack member 54 and the outer tube 16 in the proximal direction caused by a rotative operation of the operation wheel 58 in the arrow A direction, first, a first (on the distal side) stent 12 is released from the outer tube 16. Then, when the operation wheel 58 is rotatively operated further in the arrow A direction after the first stent 12 is released, a second stent 12 is released from the outer tube 16 in accordance with movements of the rack member 54 and the outer tube 16 in the proximal direction.

In this case, the two stents 12 may be continuously released without changing the position of the stent delivery system 10 (the distal end of the inner tube 14). Otherwise, the position of the stent delivery system 10 (the distal end of the inner tube 14) may be changed and the second stent 12 may be released at a different portion inside a living body lumen after the first stent 12 is released.

As described above, according to the stent delivery system 10 of the first embodiment, the rack member 54 is continuously moved in the proximal direction by the plurality of pinions 56 (56a to 56c) which are provided at intervals from each other along the extension direction of the rack member 54. Therefore, the length L1 of the rack member 54 is quite shorter than the necessary movement distance L3 of the rack member 54 (refer to FIG. 4A). In contrast, in a case of a conventional configuration in which a rack member is moved by one pinion only, since the length of the rack member needs to be set to be at least equal to or greater than the necessary movement distance thereof, the length of the rack member becomes quite long so that a grip which accommodates the rack member becomes unavoidably long as well.

In accordance with an exemplary embodiment, for example, according to the stent delivery system 10, in a case of a configuration in which a long stent 12 is released or even in a case of a configuration having a plurality of stents 12 arranged side by side in the axial direction to be released, the necessary movement distance L3 of the rack member 54 can be relatively ensured without elongating the overall length of the rack member 54. Therefore, the length of the grip 18 can be shortened to the shortened length of the rack member 54, and moreover, the tractability of the grip 18 during a procedure can be improved.

In addition, since the remaining pinions 56b and 56c are configured to rotate while being interlocked with rotations of the one pinion 56a, the total number of the operation wheels 58 may be smaller than the total number of the pinions 56 so that the stent delivery system 10 can be simply operated.

Furthermore, in a case of the first embodiment, the interlocking mechanism 63 has a plurality of the rotative portions (the pulleys 64 in the illustrated example) and at least one transmission member (the belt 66 in the illustrated example) which comes into contact with the plurality of rotative portions so as to be able to transmit power thereto. According to the aforementioned configuration, a plurality of driving rotators (the pinions 56) can be reliably interlocked with each other in a simple structure.

In the first embodiment described above, a configuration in which one belt 66 is bridged with respect to three pulleys 64 is exemplified. However, when there are three or more pulleys 64, a configuration in which a plurality of belts are bridged with respect to the three or more pulleys 64 may be employed. For example, as illustrated in FIG. 3, when there are three pulleys 64, two belts may be applied to three pulleys 64. In accordance with an exemplary embodiment, for example, one belt may be configured to be bridged with respect to the pulley 64a on the farthest distal side and the pulley 64b in the middle portion, and the other belt may be configured to be bridged with respect to the pulley 64b in the middle portion and the pulley 64c on the farthest proximal side. In this case, the pulley 64b in the middle may be a coaxially arranged two-layered pulley so that one belt and the other belt may be respectively bridged with respect to the pulleys configuring the layers.

In the first embodiment described above, the rack member 54 is exemplified as a displacement member which moves in the axial direction of the grip 18, and the plurality of pinions 56 are exemplified as a plurality of driving rotators. However, the displacement member and the driving rotators are not limited to a configuration in which the rack 55 meshes with the pinions 56 so as to transmit power. For example, a configuration in which power is transmitted due to friction resistance caused by contact between an outer side surface of the displacement member and the outer circumferential surface of each of the driving rotators may be applied thereto. The aforementioned point is similarly applied to the second to fourth embodiments described below.

Figure 5:
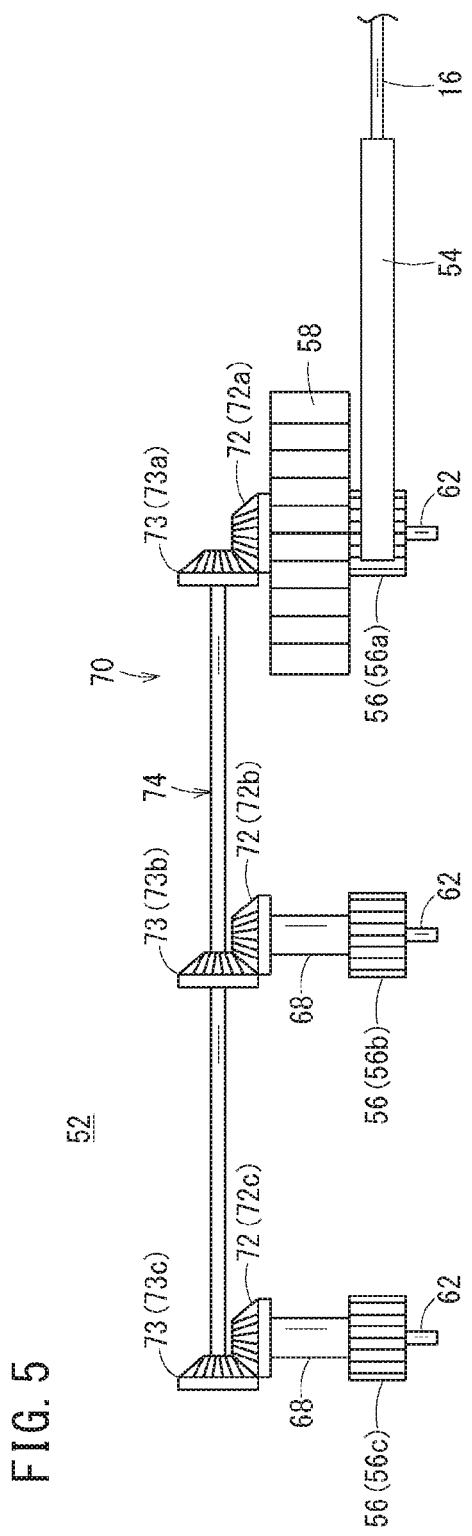
FIG. 5 is a plan view of the movement mechanism provided with an interlocking mechanism, according to a modification example.

In place of the interlocking mechanism 63 described above, an interlocking mechanism 70 illustrated in FIG. 5 may be employed. The interlocking mechanism 70 is configured to transmit power by a drive shaft 74. In accordance with an exemplary embodiment, for example, the interlocking mechanism 70 has a plurality of (three in the illustrated example) first bevel gears 72 (the rotative portions) which are coaxially and respectively provided in the plurality of pinions 56, and the drive shaft 74 (the transmission member) provided with a plurality of (three in the illustrated example) second bevel gears 73 which respectively mesh with the plurality of first bevel gears 72.

When the operation wheel 58 is rotatively operated, rotations of a first bevel gear 72a which integrally rotates with the operation wheel 58 on the farthest distal side are transmitted to remaining first bevel gears 72b and 72c via the drive shaft 74. Accordingly, the three pinions 56a to 56c being interlocked with each other rotate in the same direction in accordance with a rotative operation of the operation wheel 58.

Note that, in a case of a configuration illustrated in FIG. 5, all of the products of the number of teeth and module are equal in three first bevel gears 72a to 72c, and all of the products of the number of teeth and module are equal in three second bevel gears 73a to 73c. Accordingly, when the three pinions 56a to 56c rotate while being interlocked with each other, all of the rotational speeds of the pinions 56a to 56c are the same.

FIG. 6 is a partially omitted side view of a stent delivery system 80 according to the second embodiment of the present disclosure. In FIG. 6, the proximal portion of the inner tube 14 and the grip 18 (the housing 50) are indicated by a virtual line. Note that, in the stent delivery system 80 according to the second embodiment, the same reference numbers are applied to elements exhibiting the function and the effect which are the same as or similar to those of the stent delivery system 10 according to the first embodiment, and detailed description thereof will be omitted.

In accordance with an exemplary embodiment, the stent delivery system 80 is different from the stent delivery system 10 according to the first embodiment described above, in the configuration of an interlocking mechanism 82. The interlocking mechanism 82 has a plurality of pulleys 84 (the rotative portions) which are coaxially and respectively provided in the plurality of pinions 56, and at least one belt 86 (the transmission member) which comes into contact with the plurality of pulleys 84 so as to be able to transmit power thereto.

In the present embodiment, among the plurality of pulleys 84, a pulley 84a on the farthest distal side has the greatest diameter, and a pulley 84c on the farthest proximal side has the smallest diameter. Accordingly, the diameter of the pulley 84c on the farthest proximal side is smaller than the diameter of the pulley 84a on the farthest distal side. The diameter of a pulley 84b provided in the middle portion is smaller than the diameter of the pulley 84a on the farthest distal side and is greater than the diameter of the pulley 84c on the farthest proximal side.

In the present embodiment, each of the pulleys 84 is a toothed pulley, and each of the pulleys 84 meshes with the belt 86. In accordance with an exemplary embodiment, all of the modules of the pulleys 84 are equal. However, as described above, since the diameter of the pulley 84c on the farthest proximal side is smaller than the diameter of the pulley 84a on the farthest distal side, the number of teeth of the pulley 84c on the farthest proximal side is smaller than the number of teeth of the pulley 84a on the farthest distal side. The number of teeth of the pulley 84b provided in the middle portion is smaller than the number of teeth of the pulley 84a on the farthest distal side and is greater than the number of teeth of the pulley 84c on the farthest proximal side.

In accordance with an exemplary embodiment, the belt 86 is a flexible endless member (an annular member) and can be configured to be formed with a resin material, for example. The belt 86 can be bridged between the plurality of pulleys 84. Specifically, the belt 86 is wound around both the pulleys 84a and 84c on the farthest distal side and the farthest proximal side and comes into contact with the outer circumferential portions (an upper portion and a lower portion) of the pulley 84b which is provided in the middle portion.

Note that, it can be preferable that the belt 86 comes into contact with at least a part of the pulley 84b which is provided in the middle portion. For example, the belt 86 may come into contact with only the upper portion or only the lower portion of the pulley 84b. Each pulley 84 and the belt 86 may be a flat pulley and a flat belt having no tooth formed therein. Otherwise, each pulley 84 and the belt 86 may also be a V-pulley and a V-belt.

In the interlocking mechanism 82 having the aforementioned configuration, when the plurality of pulleys 84 are interlocked with each other by the belt 86, the pulley 84c on the farthest proximal side rotates faster than the pulley 84a on the farthest distal side. In other words, rotations of the pulley 84a on the farthest distal side can be accelerated and transmitted to the pulley 84c on the farthest proximal side. Accordingly, in a case where rotative operation speeds are the same as each other with respect to the operation wheel 58, when the rack member 54 is driven by the pinion 56a on the farthest distal side, the movement speed of the outer tube 16 which moves together with the rack member 54 is relatively slow. When the rack member 54 is driven by the pinion 56c on the farthest proximal side, the movement speed of the outer tube 16 which moves together with the rack member 54 is relatively fast.

According to the stent delivery system 80, when the operation wheel 58 is rotatively operated, the rack member 54 is moved continuously in the proximal direction by the plurality of pinions 56 which rotate while being interlocked with an operation of the interlocking mechanism 82. Thus, the outer tube 16 can be moved in the proximal direction with respect to the inner tube 14. At a stage where the stent 12 is gradually released from the distal end side thereof in accordance with a movement of the outer tube 16 in the proximal direction and the rack member 54 is moved to a position depicted with the dotted line in FIG. 6, the stent 12 can be completely released from the distal end of the outer tube 16.

In this case, the rack member 54 is moved by the pinion 56a on the farthest distal side at a low speed in the proximal direction at the initial stage of releasing the stent 12. Therefore, the stent 12 is slowly released, thereby being relatively easy to position. Meanwhile, the rack member 54 is moved in the proximal direction by the pinion 56c on the farthest proximal side at the final stage of releasing the stent 12. Since the rotational speed of the pulley 84c on the farthest proximal side is accelerated with respect to the pulley 84a on the farthest distal side, the stent 12 can be promptly released at the end stage of releasing the stent 12. Thus, the procedure can finish relatively early.

Similar to the first embodiment, in the second embodiment as well, the rack member 54 is driven by the plurality of pinions 56 which are arranged at intervals in the extension direction of the rack member 54. Therefore, the rack member 54 can have a quite short length L1 compared to the necessary movement distance L3 of the rack member 54. Accordingly, even in a case of a configuration having a long stent 12 or the plurality of stents 12 arranged side by side in the axial direction to be released, there is no need to increase the rack member 54 in length and size. As a result thereof, the length of the grip 18 can be shortened and the tractability of the grip 18 during a procedure can be improved.

In the second embodiment described above, a configuration in which one belt 86 is bridged between three pulleys 84 is exemplified. However, when there are three or more pulleys 84, a configuration can be employed in which a plurality of belts are bridged between the three or more pulleys 84. For example, as illustrated in FIG. 6, when there are three pulleys 84, one belt may be configured to be bridged between the pulley 84a on the farthest distal side and the pulley 84b in the middle portion, and the other belt may be configured to be bridged between the pulley 84b in the middle portion and the pulley 84c on the farthest proximal side. In this case, the pulley 84b in the middle portion may be a coaxially arranged as two-layered pulley so that one belt and the other belt may be respectively hung with respect to the pulleys configuring the layers.

Moreover, in the second embodiment, it is natural for each of the configuration portions in common with that of the first embodiment to be able to attain the operation and the effect which are the same as or similar to the operation and the effect of each of the configuration portions of the first embodiment in common.

FIG. 7 is a partially omitted side view of a stent delivery system 90 according to the third embodiment of the present disclosure. In FIG. 7, the proximal portion of the inner tube 14 and a grip 78 (the housing 50) are indicated by a virtual line. Note that, in the stent delivery system 90 according to the third embodiment, the same reference numbers are applied to elements exhibiting the function and the effect which are the same as or similar to those of the stent delivery system 10 according to the first embodiment, and detailed description thereof will be omitted.

The stent delivery system 90 is provided with the grip 78 having a movement mechanism 52a for moving the outer tube 16 in the proximal direction with respect to the inner tube 14. The movement mechanism 52a has the rack member 54, a plurality of pinions 92 and 94, a plurality of operation wheels 96 and 98, and an interlocking mechanism 100. The total number of the operation wheels 96 and 98 is smaller than the total number of the pinions 92 and 94. The rack member 54 is provided with a first rack 102 (a first driven portion) and a second rack 104 (a second driven portion) which extend in a parallel manner on sides opposite to each other (the upper side and the lower side in the illustrated example).

The plurality of pinions 92 and 94 have a plurality of first pinions 92 (the driving rotators) which can mesh with the first rack 102 and are arranged at intervals in the extension direction of the rack member 54, and a plurality of second pinions 94 (the driving rotators) which can mesh with the second rack 104 and are arranged at intervals in the extension direction of the rack member 54.

In the present embodiment, the product of the number of teeth and the module of each second pinion 94 is greater than the product of the number of teeth and the module of each first pinion 92. Therefore, a movement distance per unit rotation angle of each second pinion 94 in the rack member 54 is greater than a movement distance per unit rotation angle of each first pinion 92 in the rack member 54. In accordance with an exemplary embodiment, for example, when the rotation angles thereof are the same as each other, the movement distance of the rack member 54 driven by the second pinions 94 is greater than the movement distance of the rack member 54 driven by the first pinions 92.

Accordingly, in a case where a rotative operation speed with respect to a first operation wheel 96 and a rotative operation speed with respect to a second operation wheel 98 are the same as each other, when the first operation wheel 96 is rotatively operated, the movement speed of the outer tube 16, which moves together with the rack member 54 can be relatively slow. When the second operation wheel 98 is rotatively operated, the movement speed of the outer tube 16, which moves together with the rack member 54 can be relatively fast.

The plurality of operation wheels 96 and 98 include the first operation wheel 96 and the second operation wheel 98 which are partially exposed on outer side surfaces (the top surface and the bottom surface in FIG. 7) of the grip 78 on sides opposite to each other via the opening portions 39. In the present illustrated example, a first pinion 92*a* on the distal side is provided in the first operation wheel 96, and a second pinion 94*a* on the farthest distal side is provided in the second operation wheel 98.

Note that, the first operation wheel 96 may be provided so as to integrally rotate with a first pinion 92*b* on the proximal side. In addition, the second operation wheel 98 may be provided so as to integrally rotate with a second pinion 94*b* in the middle portion or a second pinion 94*c* on the farthest proximal side.

In accordance with an exemplary embodiment, the length L1 of the rack member 54 (both the lengths of the first rack 102 and the second rack 104) is greater than a center-to-center distance L4 between the first pinions 92 and is greater than a center-to-center distance L5 between the second pinions 94. The rack member 54 meshes with at least one of the first pinions 92 and meshes with at least one of the second pinions 94 within the movable range of the rack member 54.

Note that, the numbers of teeth and the modules are the same as each other in the plurality of first pinions 92 (92*a* and 92*b*), and the numbers of teeth and the modules are the same as each other in the plurality of second pinions 94 (94*a* to 94*c*). The modules of the first pinions 92 and the second pinions 94 may be the same as each other. However, in this exemplary embodiment, as illustrated in FIG. 7, the number of teeth of each second pinion 94 is greater than the number of teeth of each first pinion 92. In accordance with an exemplary embodiment, for example, the number of teeth of each first pinion 92 and the number of teeth of each second pinion 94 may be the same as each other, and the module of each second pinion 94 may be greater than the module of each first pinion 92. Moreover, the number of teeth and the module of each second pinion 94 may be respectively greater than the number of teeth and the module of each first pinion 92.

The interlocking mechanism 100 has a first interlocking portion 106 which interlocks the plurality of first pinions 92 with each other, and a second interlocking portion 108 which interlocks the plurality of second pinions 94 with each other.

The first interlocking portion 106 has a plurality of first pulleys 110 (first rotative portions) which are coaxially and respectively provided in the plurality of first pinions 92, and a first belt 112 (a first transmission member) which comes into contact with the plurality of first pulleys 110 so as to be able to transmit power thereto. In the illustrated example, a first pulley 110*a* on the distal side is provided on a side opposite to the first pinion 92*a* in the first operation wheel 96. Accordingly, the first operation wheel 96, the first pinion 92*a*, and the first pulley 110*a* are coaxially arranged so as to integrally rotate.

A first pulley 110*b* on the proximal side is coaxially connected to the first pinion 92*b* on the proximal side via a connection shaft similar to the connection shaft 68 illustrated in FIG. 3. Accordingly, the first pulley 110*b* and the first pinion 92*b* on the proximal side integrally rotate. In the present embodiment, all of the diameters of the plurality of first pulleys 110 are equal to each other. Accordingly, when the plurality of first pulleys 110 rotate while being interlocked with each other by the first belt 112, all of the rotational speeds of the plurality of first pulleys 110 are equal.

In accordance with an exemplary embodiment, the first belt 112 is a flexible endless member (an annular member) and can be configured to be formed with a resin material, for example. The first belt 112 is wound around the first pulley 110*a* on the distal side and the first pulley 110*b* on the proximal side. In the present illustrated example, each first pulley 110 is a toothed pulley, and the first belt 112 is a toothed belt. Note that, each first pulley 110 and the first belt 112 may be a flat pulley and a flat belt having no tooth formed therein. In accordance with an exemplary embodiment, for example, each first pulley 110 and the first belt 112 may also be a V-pulley and a V-belt.

Due to the aforementioned configuration of the first interlocking portion 106, when the first operation wheel 96 is rotatively operated, rotations of the first pulley 110*a* on the distal side are transmitted to the first pulley 110*b* on the proximal side via the first belt 112. Accordingly, the plurality of first pinions 92 can rotate while being interlocked with each other and the rack member 54 can thereby move forward or rearward by only rotatively operating one first operation wheel 96.

The second interlocking portion 108 has a plurality of second pulleys 114 (second rotative portion) which are coaxially and respectively provided in the plurality of second pinions 94, and a second belt 116 (a second transmission member) which comes into contact with the plurality of second pulleys 114 so as to be able to transmit power thereto.

In the present illustrated example, a second pulley 114*a* on the farthest distal side is provided on a side opposite to the second pinion 94*a* in the second operation wheel 98. Accordingly, the second operation wheel 98, the second pinion 94*a*, and the second pulley 114*a* are coaxially arranged so as to integrally rotate.

Remaining second pulleys 114*b* and 114*c* are respectively connected to the remaining second pinions 94*b* and 94*c* via a connection shaft similar to the connection shaft 68 illustrated in FIG. 3. The second pinion 94*b* and the second pulley 114*b* which are provided in the middle portion integrally rotate. The second pinion 94*c* and the second pulley 114*c* which are provided on the farthest proximal side integrally rotate.

In the present embodiment, all of the diameters of the plurality of second pulleys 114 are equal to each other. Accordingly, when the plurality of second pulleys 114 rotate while being interlocked with each other by the second belt 116, all of the rotational speeds of the plurality of second pulleys 114 are equal.

The second belt 116 is a flexible endless member (an annular member) and can be configured to be formed with a resin material, for example. In the present illustrated example, the second belt 116 is wound around the second pulley 114*a* on the farthest distal side and the second pulley 114*c* on the farthest proximal side and comes into contact with the outer circumferential portions (an upper portion and a lower portion) of the second pulley 114*b* which is provided in the middle portion. Note that, it can be preferable that the second belt 116 comes into contact with at least a part of the second pulley 114*b* which is provided in the middle portion. For example, the second belt 116 may come into contact with only the upper portion or only the lower portion of the second pulley 114*b*.

In the present illustrated example, each second pulley 114 is a toothed pulley, and the second belt 116 is a toothed belt. Note that, each second pulley 114 and the second belt 116 may be a flat pulley and a flat belt having no tooth formed therein. In accordance with an exemplary embodiment, for example, each second pulley 114 and the second belt 116 may also be a V-pulley and a V-belt.

Due to the aforementioned configuration of the second interlocking portion 108, when the second operation wheel 98 is rotatively operated, rotations of the second pulley 114*a* on the farthest distal side are transmitted to the second pulley 114b provided in the middle portion and the second pulley 114c on the farthest proximal side via the second belt 116. Accordingly, the plurality of second pinions 94 can rotate while being interlocked with each other and the rack member 54 can thereby move forward or rearward by only rotatively operating one second operation wheel 98.

According to the stent delivery system 90 having the aforementioned configuration, when the first operation wheel 96 or the second operation wheel 98 is rotatively operated in the arrow A direction, the plurality of pinions 92 and 94 rotate so that the rack member 54 is moved continuously in the proximal direction. Thus, the outer tube 16 can move in the proximal direction with respect to the inner tube 14. At a stage where the stent 12 is gradually released from the distal end side thereof in accordance with a movement of the outer tube 16 in the proximal direction and the rack member 54 is moved to a position depicted with the dotted line in FIG. 7, the stent 12 is completely released from the distal end of the outer tube 16.

In this case, the first pinions 92 and the second pinions 94 are different from each other in speed of moving the rack member 54. Therefore, a release speed of the stent 12 from the outer tube 16 can be easily controlled by rotatively operating the first operation wheel 96 or the second operation wheel 98 in the arrow A direction so as to rotate the first pinions 92 or the second pinions 94 in accordance with an intended speed of releasing the stent 12.

For example, when the stent 12 is intended to be slowly released, the first operation wheel 96 may be rotatively operated so as to cause the first pinions 92 having less teeth to drive the rack member 54. Then, the outer tube 16 is moved in the proximal direction at a low speed. Meanwhile, when the stent 12 is intended to be promptly released, the second operation wheel 98 may be rotatively operated so as to cause the second pinions 94 having more teeth to drive the rack member 54. Then, the outer tube 16 is moved in the proximal direction at a high speed.

In addition, for example, in a case of a long stent 12, the first pinions 92 drive the rack member 54 by rotatively operating the first operation wheel 96 at the initial stage of releasing the stent 12. Then, the outer tube 16 is moved in the proximal direction. Consequently, the stent 12 is slowly released, thereby being easy to be positioned. Meanwhile, the second operation wheel 98 is rotatively operated so as to cause the second pinions 94 to drive the rack member 54 at the final stage of releasing the stent 12. Then, the outer tube 16 moves in the proximal direction. Consequently, the stent 12 is promptly released. Thus, the procedure can finish early.

Similar to the first embodiment, in the third embodiment as well, the rack member 54 is driven by the plurality of pinions 92 and 94 which are arranged at intervals in the extension direction of the rack member 54. Therefore, the rack member 54 can have a quite short length L1 compared to the necessary movement distance L3 of the rack member 54. Accordingly, even in a case of a configuration having a long stent 12 or the plurality of stents 12 arranged side by side in the axial direction to be released, there is no need to increase the rack member 54 in length and size. As a result thereof, the length of the grip 78 can be shortened and the tractability of the grip 78 during a procedure can be improved.

In addition, according to the third embodiment, the first pinions 92 and the second pinions 94 are different from each other in speed of moving the rack member 54. Therefore, a release speed of the stent 12 from the outer tube 16 can be easily controlled by rotating the first pinions 92 or the second pinions 94 in accordance with an intended speed of releasing the stent 12.

In addition, according to the third embodiment, since the first pinions 92 and the second pinions 94 are arranged on sides opposite to each other while having the rack member 54 as a reference, the first pinions 92 and the second pinions 94 which are respectively provided to be plural in number can be efficiently arranged inside the grip 78.

Furthermore, according to the third embodiment, since the first operation wheel 96 and the second operation wheel 98 are exposed from the grip 78 on sides different from each other, it can be relatively easy for a user to discriminate between the first operation wheel 96 and the second operation wheel 98, which are thereby suitably and easily used.

In a case of the third embodiment, the first interlocking portion 106 has a plurality of first rotative portions (the first pulleys 110 in the illustrated example), and at least one first transmission member (the first belt 112 in the illustrated example) which comes into contact with the plurality of first rotative portions so as to be able to transmit power thereto. According to the aforementioned configuration, the plurality of first driving rotators (the first pinions 92) can be reliably interlocked with each other in simple structure. In addition, the second interlocking portion 108 has a plurality of second rotative portions (the second pulleys 114 in the illustrated example), and at least one second transmission member (the second belt 116 in the illustrated example) which comes into contact with the plurality of second rotative portions so as to be able to transmit power thereto. According to the aforementioned configuration, the plurality of second driving rotators (the second pinions 94) can be reliably interlocked with each other in a simple structure.

In a case of the third embodiment, since the first interlocking portion 106 and the second interlocking portion 108 are individually configured to be belt mechanisms, power can be efficiently transmitted, and the rack member 54 can smoothly move forward or rearward by rotatively operating the first operation wheel 96 or the second operation wheel 98.

Moreover, in the third embodiment, it can be natural for each of the configuration portions in common with that of the first embodiment to be able to attain the operation and the effect which are the same as or similar to the operation and the effect of each of the configuration portions of the first embodiment in common.

In the third embodiment described above, a configuration in which one second belt 116 is bridged between three second pulleys 114 is exemplified. However, when there are three or more second pulleys 114, a configuration in which the plurality of second belts are bridged between the three or more second pulleys 114 may be employed. For example, as illustrated in FIG. 7, when there are three second pulleys 114, two second belts may be applied to three second pulleys 114. Specifically, one second belt may be configured to be bridged between the second pulley 114a on the farthest distal side and the second pulley 114b in the middle portion, and the other second belt may be configured to be bridged between the second pulley 114b in the middle portion and the second pulley 114c on the farthest proximal side. In this case, the second pulley 114b in the middle may be a coaxially arranged as a two-layered pulley so that one second belt and the other second belt may be respectively bridged with respect to the pulleys configuring the layers.

Note that, even though two first pulleys 110 are illustrated in FIG. 7, when three or more first pulleys 110 are provided, a plurality of first belts may be configured to be hung with respect to the three or more first pulleys 110.

In the configuration illustrated in FIG. 7, in accordance with an exemplary embodiment, the product of the number of teeth and the module of each second pinion 94 is greater than the product of the number of teeth and the module of each first pinion 92. However, in contrast with the aforementioned configuration, the product of the number of teeth and the module of each first pinion 92 may be greater than the product of the number of teeth and the module of each second pinion 94. In this case, the stent 12 can be promptly released when the first operation wheel 96 provided with the first pinion 92 is rotatively operated, and the stent 12 is slowly released when the second operation wheel 98 provided with the second pinion 94 is rotatively operated.

In the configuration illustrated in FIG. 7, two racks (the first rack 102 and the second rack 104) are provided as the rack member 54, and the plurality of first pinions 92 and the plurality of second pinions 94 are arranged in a movement path of the rack member 54 on sides opposite to each other. However, the configuration may have the below-described arrangement. In accordance with an exemplary embodiment, for example, only one rack may be provided as the rack member 54, and the plurality of first pinions 92 and the plurality of second pinions 94 may be provided on the same side with respect to the movement path of the rack member 54. In this case, the plurality of first pinions 92 and the plurality of second pinions 94 can be alternately arranged along the axial direction of the rack member 54.

FIG. 8 is a partially omitted side view of a stent delivery system 120 according to the fourth embodiment of the present disclosure. In FIG. 8, the proximal end portion of the inner tube 14 and a grip 122 (the housing 50) are indicated by a virtual line. Note that, in the stent delivery system 120 according to the fourth embodiment, the same reference numbers are applied to elements exhibiting the function and the effect which are the same as or similar to those of the stent delivery system 10 according to the first embodiment, and detailed description thereof will be omitted.

The stent delivery system 120 is provided with the grip 122 which has a movement mechanism 52b for moving the outer tube 16 in the proximal direction with respect to the inner tube 14. The movement mechanism 52b has the rack member 54, a plurality of (three in the illustrated example) pinions 124, a plurality of (two in the illustrated example) operation wheels 126, and an interlocking mechanism 128. In accordance with an exemplary embodiment, the total number of the operation wheels 126 is smaller than the total number of the pinions 124. The rack member 54 is provided with the first rack 102 and the second rack 104 on sides opposite to each other (the upper side and the lower side in the illustrated example).

In accordance with an exemplary embodiment, the plurality of pinions 124 are arranged at intervals from each other in the extension direction of the rack member 54. For example, the plurality of pinions 124 have a plurality of first pinions 124a (the driving rotators) which can mesh with the first rack 102 and which are arranged at intervals in the extension direction of the rack member 54, and a second pinion 124b (the driving rotator) which can mesh with the second rack 104. The second pinion 124b is arranged on a proximal side farther than the first pinion 124a on the proximal side.

The plurality of operation wheels 126 are rotatably arranged at intervals in the extension direction (in the axial direction) of the rack member 54. The plurality of operation wheels 126 include a first operation wheel 126a which drives the rack member 54 via the first rack 102, and a second operation wheel 126b which drives the rack member 54 via the second rack 104.

In the illustrated example, one first operation wheel 126a is provided, and one second operation wheel 126b is provided. The first operation wheel 126a and the second operation wheel 126b are partially exposed on the outer side surfaces (the top surface and the bottom surface in FIG. 8) of the grip 122 on sides opposite to each other via the opening portions 39.

In the present illustrated example, the first operation wheel 126a is provided so as to integrally rotate with the first pinion 124a on the distal side. Note that, the first operation wheel 126a may be provided so as to integrally rotate with the first pinion 124a on the proximal side. The second operation wheel 126b is provided with the second pinion 124b.

The product of the number of teeth and the module of the second pinion 124b is greater than the product of the number of teeth and the module of each first pinion 124a. Therefore, a movement distance per unit rotation angle of the second pinion 124b in the rack member 54 is greater than a movement distance per unit rotation angle of each first pinions 124a in the rack member 54. In accordance with an exemplary embodiment, for example, when the rotation angles thereof are the same as each other, the movement distance of the rack member 54 driven by the second pinion 124b is greater than the movement distance of the rack member 54 driven by the first pinions 124a.

Accordingly, in a case where a rotative operation speed with respect to the first operation wheel 126a and a rotative operation speed with respect to the second operation wheel 126b are the same as each other, when the first operation wheel 126a is rotatively operated, the movement speed of the outer tube 16 which moves together with the rack member 54 is relatively slow. When the second operation wheel 126b is rotatively operated, the movement speed of the outer tube 16, which moves together with the rack member 54 is relatively fast.

The numbers of teeth and the modules are the same as each other in the plurality of first pinions 124a. The modules of the first pinions 124a and the second pinion 124b may be the same as each other. However, in this case, as illustrated in FIG. 8, the number of teeth of the second pinion 124b is greater than the number of teeth of each first pinion 124a. Otherwise, the number of teeth of each first pinion 124a and the number of teeth of the second pinion 124b may be the same as each other, and the module of the second pinion 124b may be greater than the module of each first pinion 124a. Moreover, the number of teeth and the module of the second pinion 124b may be respectively greater than the number of teeth and the module of each first pinion 124a.

The length (the length of both the first rack 102 and the second rack 104) L1 of the rack member 54 is greater than a center-to-center distance L6 between the first pinions 124a. In addition, the length L1 of the rack member 54 is greater than a center-to-center distance L7 between the first pinion 124a on the proximal side and the second pinion 124b. Accordingly, the rack member 54 meshes with at least two adjacent pinions 124 among the plurality of pinions 124 in the axial direction of the grip 122 (in the extension direction of the rack member 54) within the movable range of the rack member 54. Note that, the center-to-center distance L6 between the first pinions 124a, and the center-to-center distance L7 between the first pinion 124a on the proximal side and the second pinion 124b may be the same as each other or may be different from each other.

The interlocking mechanism 128 has a plurality of pulleys 130 (the rotative portions) which are coaxially and respectively provided in the plurality of first pinions 124a, and a belt 132 (the transmission member) which comes into contact with the plurality of pulleys 130 so as to be able to transmit power thereto. In the illustrated example, a pulley 130a on the distal side is provided on a side opposite to the first pinion 124a in the first operation wheel 126a. Accordingly, the first operation wheel 126a, the first pinion 124a, and the pulley 130a are coaxially arranged so as to integrally rotate.

A pulley 130b on the proximal side is coaxially connected to the first pinion 124a on the proximal side via a connection shaft similar to the connection shaft 68 illustrated in FIG. 3. Accordingly, the pulley 130b on the proximal side and the first pinion 124a on the proximal side integrally rotate. In the present embodiment, all of the diameters of the plurality of pulleys 130 are equal to each other. Accordingly, when the plurality of pulleys 130 rotate while being interlocked with each other by the belt 132, all of the rotational speeds of the plurality of pulleys 130 are equal.

The belt 132 is a flexible endless member (an annular member) and can be configured to be formed with a resin material, for example. The belt 132 is wound around the pulley 130a on the distal side and the pulley 130b on the proximal side. In the present illustrated example, each pulley 130 is a toothed pulley, and the belt 132 is a toothed belt. Note that, each pulley 130 and the belt 132 may be a flat pulley and a flat belt having no tooth formed therein. In accordance with an exemplary embodiment, for example, each pulley 130 and the belt 132 may also be a V-pulley and a V-belt.

Due to the aforementioned configuration of the interlocking mechanism 128, when the first operation wheel 126a is rotatively operated, rotations of the pulley 130a on the distal side are transmitted to the pulley 130b on the proximal side via the belt 132. Accordingly, the plurality of first pinions 124a can rotate while being interlocked with each other and the rack member 54 can thereby move forward or rearward by only rotatively operating one first operation wheel 126a.

According to the stent delivery system 120 having the aforementioned configuration, when the operation wheels 126 is rotatively operated in the arrow A direction, the plurality of pinions 124 rotate so that the rack member 54 is moved continuously in the proximal direction. Thus, the outer tube 16 can be moved in the proximal direction with respect to the inner tube 14. At a stage where the stent 12 is gradually released from the distal end side thereof in accordance with a movement of the outer tube 16 in the proximal end direction and the rack member 54 is moved to a position depicted with the dotted line in FIG. 8, the stent 12 is completely released from the distal end of the outer tube 16.

In this case, the first operation wheel 126a is rotatively operated so as to cause the first pinion 124a on the distal side to move the rack member 54 at a low speed in the proximal direction at the initial stage of releasing the stent 12. Therefore, the stent 12 is slowly released, thereby being easy to be positioned. Meanwhile, the second operation wheel 126b is rotatively operated so as to cause the second pinion 124b to move the rack member 54 at a high speed in the proximal direction at the final stage of releasing the stent 12. Therefore, the stent 12 is promptly released. Thus, the procedure can end early.

Similar to the first embodiment, in the fourth embodiment as well, the rack member 54 is driven by the plurality of pinions 124 which are arranged at intervals in the extension direction of the rack member 54. Therefore, the rack member 54 can have a quite short length L1 compared to the necessary movement distance L3 of the rack member 54. Accordingly, even in a case of a configuration having a long stent 12 or the plurality of stents 12 arranged side by side in the axial direction to be released, there is no need to increase the rack member 54 in length and size. As a result thereof, the length of the grip 122 can be shortened and the tractability of the grip 122 during a procedure can be improved.

In addition, according to the fourth embodiment, since the first operation wheel 126a and the second operation wheel 126b are exposed from the grip 122 on sides different from each other, it is relatively easy for a user to discriminate between the first operation wheel 126a and the second operation wheel 126b, which are thereby suitably and easily used.

Moreover, in the fourth embodiment, it is natural for each of the configuration portions in common with that of the first embodiment to be able to attain the operation and the effect which are the same as or similar to the operation and the effect of each of the configuration portions of the first embodiment in common.

Note that, in the configuration illustrated in FIG. 8, two racks (the first rack 102 and the second rack 104) are provided in the rack member 54, and the first pinions 124a and the second pinion 124b are arranged in the movement path of the rack member 54 on sides opposite to each other. However, the configuration may have the below-described arrangement. In accordance with an exemplary embodiment, for example, there may be provided only one rack in the rack member 54, and the first pinions 124a and the second pinion 124b may be provided on the same side with respect to the movement path of the rack member 54.

Figure 9:
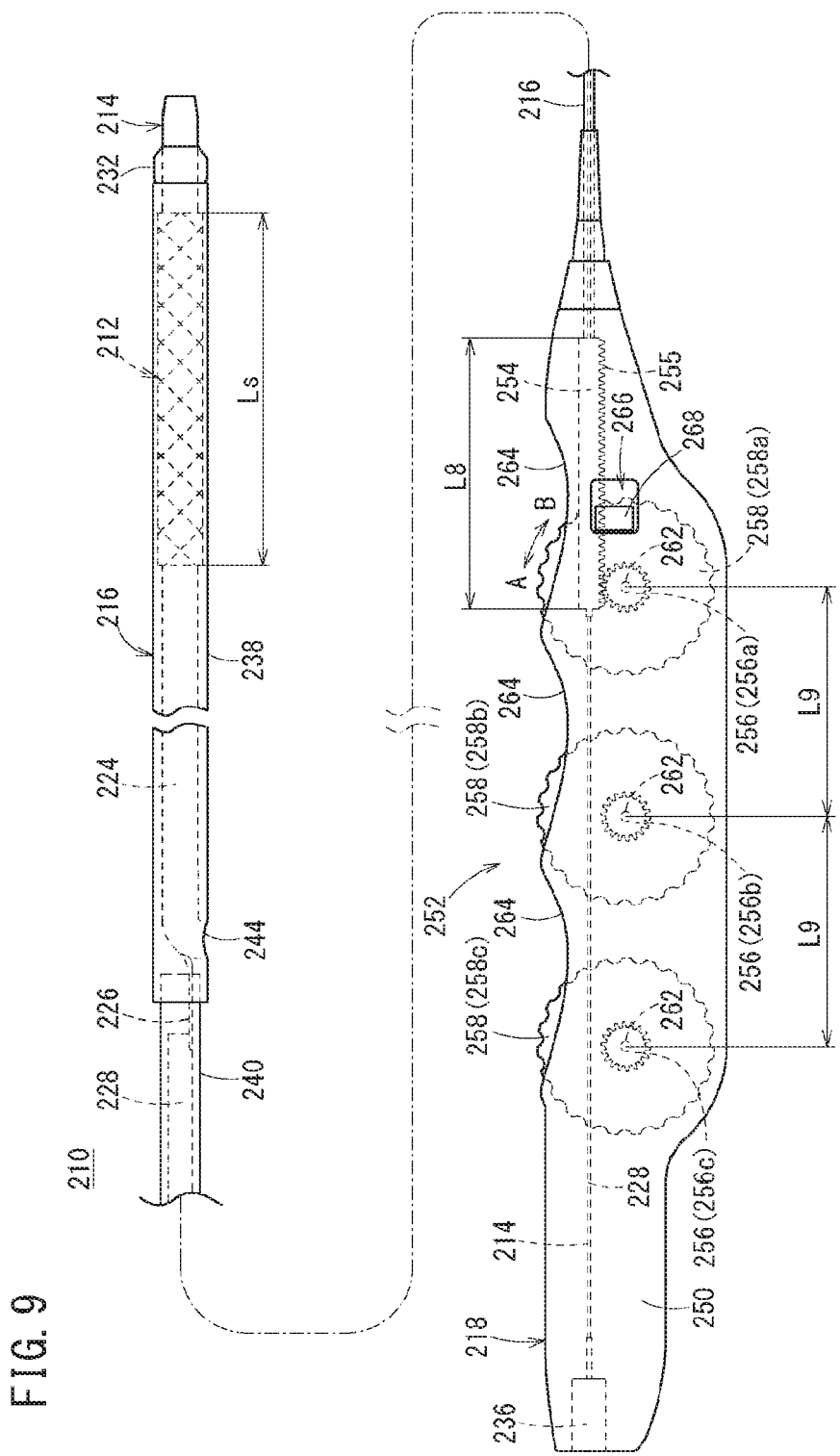
FIG. 9 is a partially omitted side view of a stent delivery system according to a fifth embodiment of the present disclosure.
Figure 14:
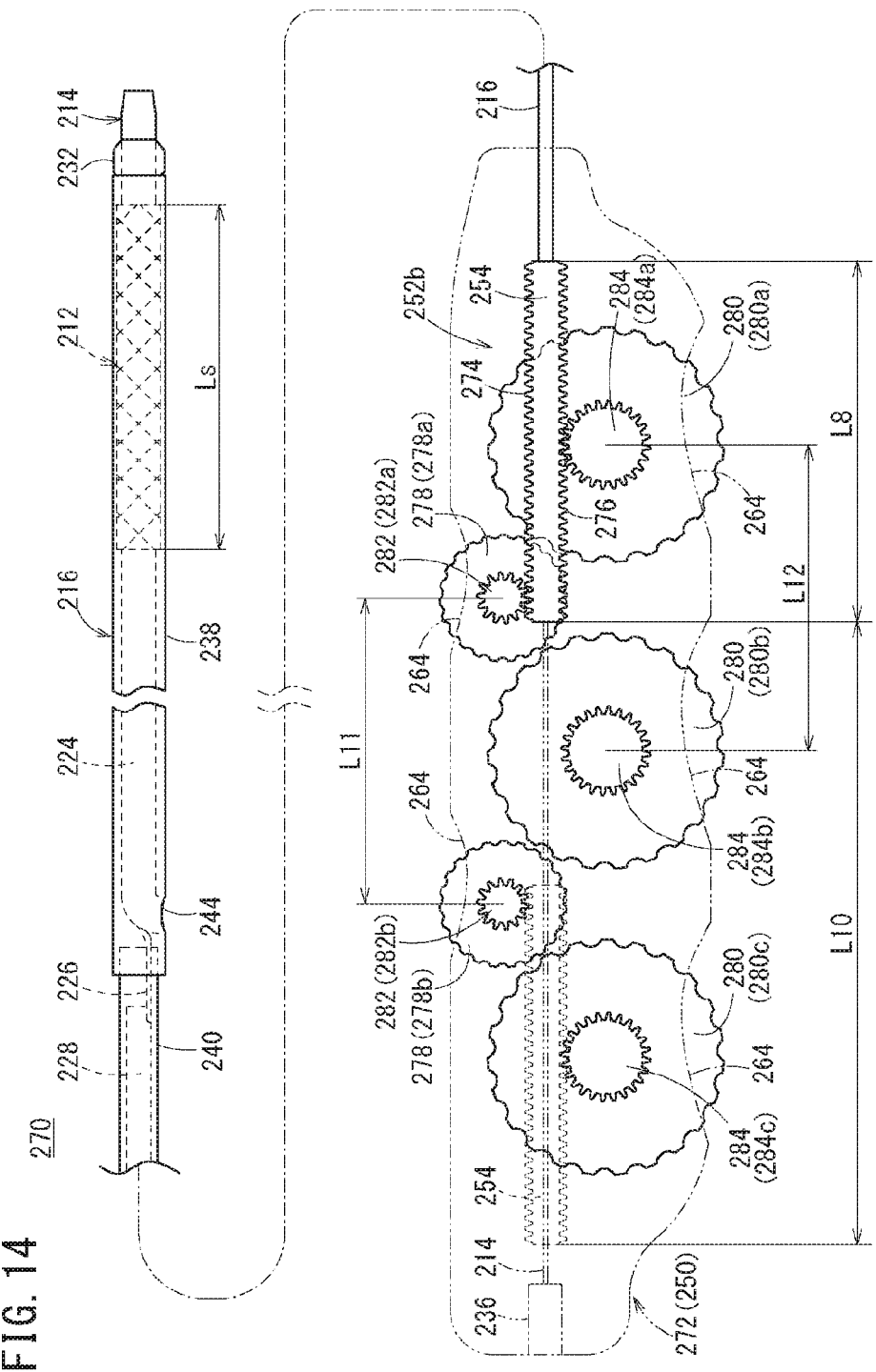
FIG. 14 is a partially omitted side view of a stent delivery system according to a sixth embodiment of the present disclosure.

FIG. 9 is a partially omitted side view of a stent delivery system 210 according to the fifth embodiment of the present disclosure. In FIG. 9, for convenience of illustration, illustration of an intermediate portion of the stent delivery system 210 in the axial direction is omitted, and a distal side (a stent 212 side) of the stent delivery system 210 is depicted to be greater than a proximal side (a grip 218 side) thereof. Note that, the aforementioned point is similarly applied to FIGS. 14 and 15 illustrating sixth and seventh embodiments.

The stent delivery system 210 is a medical device for delivering the stent 212 to a desired position inside a living body lumen such as a blood vessel, the bile duct, the trachea, the esophagus, the urethra, and the like and making the stent to indwell therein. The stent delivery system 210 is provided with an inner tube 214 (an inner member), an outer tube 216 (a sheath) which is arranged outside the inner tube 214, the self-expandable stent 212 which arranged between the inner tube 214 and the outer tube 216, and the grip 218 which is provided on the proximal end side of the outer tube 216.

Regarding the stent delivery system 210 in FIG. 9, a side or a direction provided with the grip 218 is referred to as "the proximal side" or "the proximal direction", and the opposite side or the opposite direction thereof is referred to as "the distal side" or "the distal direction". The same is applied to those in other diagrams.

Figure 10:
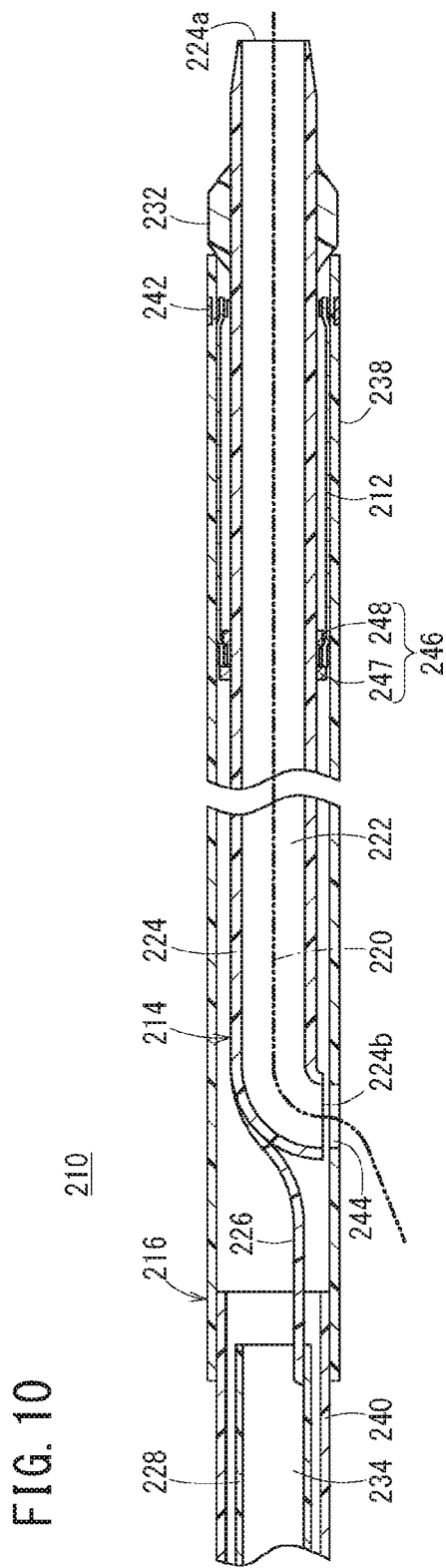
FIG. 10 is a partially omitted longitudinal sectional view of an inner tube and an outer tube in the stent delivery system illustrated in FIG. 9.

As illustrated in FIG. 10, the inner tube 214 has an inner distal tube 224 in which a guide wire lumen 222 for allowing a guide wire 220 to be inserted therethrough is formed, and an inner proximal tube 228 which is connected to the proximal end of the inner distal tube 224 via a connection member 226. The distal end of the inner tube 214, that is, the distal end of the inner distal tube 224 protrudes toward the distal end side farther than the distal end of the outer tube 216.

A distal end opening 224a which is open in the distal direction is formed at the distal end of the inner distal tube 224. The proximal end of the inner distal tube 224 is curved radially to the outside of the inner distal tube 224, and a proximal end opening 224b which is open radially outward is formed at the proximal end thereof. In the initial state (the state in FIG. 10) of the stent delivery system 210, the proximal end opening 224b communicates with a guide wire leading-out hole 244 described below. Note that, for example, the guide wire 220 is applied in order to lead the stent delivery system 210 to a lesion inside a loving body lumen.

A stopper portion 232 which protrudes radially outward and helps prevent the outer tube 216 from moving in the distal direction is formed in a distal portion of the inner distal tube 224. Since the stopper portion 232 helps prevent the outer tube 216 from moving in the distal direction, the outer tube 216 can be prevented from protruding in the distal direction farther than the distal end of the inner tube 214.

The connection member 226 is connected to the proximal end of the inner distal tube 224 and the distal end of the inner proximal tube 228. The inner proximal tube 228 has a lumen 234, which penetrates from the distal end to the proximal end thereof. As illustrated in FIG. 9, the inner proximal tube 228 protrudes in the proximal direction farther than the proximal end of the outer tube 216 in the grip 218 and linearly extends in the grip 218.

A proximal end of the inner proximal tube 228 is connected to a connector 236 which is provided in a proximal portion of the grip 218. A liquid injector for supplying liquid such as a physiological salt solution and the like to the stent delivery system 210 can be connected to the connector 236. The proximal end of the inner proximal tube 228 and the connector 236 are fixed. Consequently, the inner tube 214 is fixed so as not to move in the axial direction with respect to the grip 218.

The aforementioned inner tube 214 can be configured to be formed with a resin material, a metal material, or the like. Note that, in accordance with an exemplary embodiment, it can be preferable that the inner distal tube 224 is configured to be formed with a material having flexibility higher than that of the inner proximal tube 228.

The outer tube 216 is provided so as to be movable in the axial direction with respect to the inner tube 214 and the grip 218. In the present illustrated example, the outer tube 216 has an outer distal tube 238 and an outer proximal tube 240 which is connected to the proximal end of the outer distal tube 238. The inner distal tube 224 of the inner tube 214 is arranged inside the outer distal tube 238.

The inner proximal tube 228 of the inner tube 214 is arranged inside the outer proximal tube 240. The proximal portion of the outer tube 216, that is, the proximal portion of the outer proximal tube 240 is inserted into the grip 218.

In accordance with an exemplary embodiment, the distal end of the outer distal tube 238 functions as a release port of the stent 212 when the stent 212 indwells in a lesion inside a living body lumen and also functions as a containing port when recovering (containing again) the stent 212 which has been released partway.

The guide wire leading-out hole 244 through which the inside and outside of the outer distal tube 238 communicate with each other is formed in the vicinity of the proximal end of the outer distal tube 238. As illustrated in FIG. 10, in the initial state of the stent delivery system 210, the proximal end opening 224b of the inner distal end tube 224 and the guide wire leading-out hole 244 communicate with each other. Accordingly, the guide wire 220 can be inserted into the guide wire lumen 222 via the distal end opening 224a of the inner distal tube 224. Furthermore, the guide wire 220 can be led out of the outer tube 216 via the proximal end opening 224b and the guide wire leading-out hole 244.

As illustrated in FIG. 10, it can be preferably that a contrast marker 242 formed with an X-ray (radiation) opaque material is provided on the outer circumferential surface of the distal portion of the outer distal tube 238.

In accordance with an exemplary embodiment, the stent 212 is formed to have a substantially cylindrical shape and to be self-expandable. For example, in the initial state of the stent delivery system 210, the stent 212 is arranged between the inner tube 214 and the outer tube 216 in a contracted state. In other words, the stent 212 is contained in the outer tube 216 in a state of being prevented from expanding by the outer tube 216 and being compressed in a radially inward direction. In addition, in accordance with a movement of the outer tube 216 in the proximal direction with respect to the inner tube 214, the stent 212 is released from the outer tube 216. Therefore, the stent 212 expands in a radially outward direction due to its own elastic restoring force. A length Ls of the stent 212 can vary depending on a treatment target site. However, the length Ls ranges approximately from 10 mm to 300 mm, for example, and it is preferable that the length Ls ranges approximately from 40 mm to 250 mm.

Note that, as a configuration of the stent 212, for example, a mesh-like configuration in which multiple side holes are provided, a configuration in which multiple circular ring bodies are connected in the axial direction, a configuration in which multiple ring bodies extending in a circumferential direction in a zigzag manner is connected in the axial direction, and the like can be exemplified. As a configurational material of the stent 212, for example, a super-elastic alloy such as a Ni—Ti alloy and the like is suitable. In accordance with an exemplary embodiment, It can be preferable that a contrast marker formed with an X-ray opaque material, for example, is provided at the distal end and the proximal end of the stent 212.

As illustrated in FIG. 10, a stent holding mechanism 246 which helps prevent the stent 212 from moving in the axial direction is provided in the outer circumferential portion of the inner tube 214 (specifically, the inner distal tube 224). The stent holding mechanism 246 has a rearward movement preventing stopper 247 which helps prevent the stent 212 from moving in the proximal direction and a forward movement preventing stopper 248 which helps prevent the stent 212 from moving in the distal direction.

In accordance with an exemplary embodiment, for example, the rearward movement preventing stopper 247 helps prevent the stent 212 from moving rearward by engaging with the proximal end of the stent 212 having a decreased diameter when the outer tube 216 is moved in the proximal direction with respect to the inner tube 214 in order to release the stent 212. The forward movement preventing stopper 248 helps prevent the stent 212 from moving forward by engaging with the proximal end of the stent 212 having a decreased diameter when the outer tube 216 is moved in the distal direction with respect to the inner tube 214 in order to cause the stent 212 which has been released partway to be contained again inside the outer tube 216.

In FIG. 9, the grip 218 configured to form the proximal portion of the stent delivery system 210 is a portion which functions as a handle so that a user grips and operates the handle with one's hand. In accordance with an exemplary embodiment, the grip 218 has a hollow housing 250 and is configured to be slightly elongated in the axial direction (a front-rear direction) of the stent delivery system 210. A movement mechanism 252 for moving the outer tube 216 in the axial direction with respect to the inner tube 214 is provided inside the housing 250.

As illustrated in FIGS. 9 and 11, the movement mechanism 252 has a rack member 254 (a displacement member) which is connected to the outer tube 216, which is movable in the axial direction of the stent delivery system 210, and which extends in the axial direction, a plurality of (three in the illustrated example) pinions 256 (driving rotators) which are arranged at intervals from each other in the extension direction of the rack member 254 and move the rack member 254 in the extension direction in accordance with rotations thereof, and a plurality of (three in the illustrated example) operation wheels 258 in which the pinions 256 are respectively provided. Note that, two pinions 256 may be provided as well as four or more thereof. In this case, two operation wheels 258 may be provided as well as four or more thereof.

The rack member 254 is supported by a guide portion (not illustrated) which is provided inside the housing 250, in a slidable manner in the axial direction (the front-rear direction of the grip 218) of the stent delivery system 210. Since the rack member 254 is fixed to the proximal end portion of the outer tube 216, the outer tube 216 also moves while being interlocked with the rack member 254. The rack member 254 (the bottom surface of the rack member 254 in the illustrated example) is provided with a rack 255 which can include a plurality of tooth portions along the axial direction of the rack member 254.

Note that, as position recognizing means for the rack member 254, the housing 250 may be configured to be formed with a transparent material partially or in its entirety. In accordance with an exemplary embodiment, the housing 250 may be partially provided with an opening for exposing the rack member 254 so that a position of the rack member 254 inside the housing 250 is visually recognizable from the outside of the housing 250. Otherwise, as another configuration of the position recognizing means, the rack member 254 may be configured to be provided with a projection so that the projection protrudes from the housing 250 via a slit provided in the housing 250, and thus, the position of the rack member 254 can be recognized based on a position of the projection.

Each of the pinions 256 (256a to 256c) can mesh with the rack 255 of the rack member 254. Rotary axis centers of the three pinions 256 are parallel to each other. In addition, the rotary axis centers of the three pinions 256 exist on a straight line, which is parallel to the rack member 254 in a movable direction (the extension direction).

In FIG. 9, both center-to-center distances L9 of two pairs of adjacent pinions 256 in the three pinions 256a to 256c are equal to each other. A length L8 (the length of the rack 255) of the rack member 254 is greater than the center-to-center distance L9 between the pinions 256. Therefore, the rack 255 can mesh with at least two adjacent pinions 256. All the numbers of teeth and modules are the same in the three pinions 256a to 256c. Note that, the module (m) is a value, which is obtained by dividing the pitch circle diameter (d) by the number of the teeth (z).

The plurality of pinions 256 are respectively provided in center portions of the plurality of operation wheels 258 (258a to 258c). The operation wheels 258a to 258c are arranged at intervals in the front-rear direction of the grip 218. As illustrated in FIG. 11, the outer circumferential portion of each of the operation wheels 258 is formed to have an antislip shape in which grooves 260 and protrusion portions 261 are alternately arranged in the circumferential direction. The operation wheels 258 respectively have shaft portions 262, which protrude in the axial direction thereof. Each of the shaft portions 262 is supported by a bearing portion, which is provided in the housing 250 on the inner side. Accordingly, each of the operation wheels 258 is rotatably supported by the housing 250.

In FIG. 9, the housing 250 is provided with a plurality of opening portions 264 for partially exposing the operation wheels 258. A user can rotatively operate the operation wheels 258 by touching exposed portions of the operation wheels 258 through the opening portions 264. In the present illustrated example, all of the opening portions 264 are provided on the same side (the upper side) of the housing 250.

The grip 218 is provided with a lock mechanism 266 which can help prevent a movement operation of the rack member 254 by preventing a rotational operation of the operation wheel 258a which is arranged on the farthest distal side among the plurality of operation wheels 258. The lock mechanism 266 has a slide member 268, which is provided on a side surface of the housing 250 in a slidable manner. The slide member 268 can move between a locked position where rotational operations of the operation wheels 258 are prevented and an unlocked position where rotational operations of the operation wheels 258 are allowed. The slide member 268 is provided with a lock pin (not illustrated) which protrudes toward the inside of the housing 250.

Meanwhile, the operation wheel 258a is provided with an engagement portion (not illustrated) (for example, a groove portion) which can engage with the lock pin. When the slide member 268 is at the locked position, the lock pin engages with the engagement portion, thereby preventing a rotational operation of the operation wheel 258a. Meanwhile, when the slide member 268 is at the unlocked position, the lock pin is separated from the engagement portion, thereby allowing a rotational operation of the operation wheel 258a.

The stent delivery system 210 according to the present embodiment basically has the aforementioned configuration. Hereinafter, operations and effects thereof will be described.

In a procedure of treating a lesion (for example, a stenosed site) which has occurred inside a living body lumen (for example, inside a blood vessel) by applying the stent delivery system 210, prior to the stent delivery system 210 being inserted into the living body lumen, the guide wire 220 is inserted into the living body lumen. Then, the distal end of the guide wire 220 is in a state of having reached the lesion inside a living body lumen.

When the aforementioned state is attained, priming for filling the insides of the inner tube 214 and the outer tube 216 in the stent delivery system 210 outside a living body with predetermined liquid (for example, a physiological salt solution or the like) is performed. In priming, first, an operator connects a liquid injection device (not illustrated) to the connector 236 which is provided in the proximal end of the grip 218 and injects the liquid such as a physiological salt solution and the like into the connector 236 through the liquid injection device. Consequently, the liquid flows toward the distal sides of the inner tube 214 and the outer tube 216, thereby flowing out from each of the distal ends of the inner tube 214 and the outer tube 216. In this manner, priming performed for the insides of the inner tube 214 and the outer tube 216 outside the living body finishes.

Subsequently, as illustrated in FIG. 10, the proximal end of the guide wire 220 exposed to the outside of the living body is inserted through the guide wire lumen 222 from the distal end of the inner tube 214, thereby being led out of the outer tube 216 through the guide wire leading-out hole 244.

Then, the inner tube 214 and the outer tube 216 are caused to move forward to the inside of the living body lumen along the guide wire 220.

Then, the distal end of the outer tube 216 is confirmed for arrival at the lesion by using the contrast marker 242. Thereafter, the slide member 268 provided in the grip 218 moves to the distal side, thereby cancelling the state of preventing rotations of the operation wheel 258a. At this moment, as illustrated in FIG. 12A, the rack member 254 is positioned on the farthest distal side within a movable range thereof. In FIG. 12A, a position of the rack member 254 when the stent 212 is in a state of being completely released from the distal end of the outer tube 216 is indicated by the dotted line. A reference number L10 indicates a necessary movement distance in the rack member 254 for completely releasing the stent 212 from the distal end of the outer tube 216.

When the state of preventing rotations of the operation wheel 258a is cancelled, the operation wheel 258a is rotated in a predetermined direction (the arrow A direction) by touching the portion of the operation wheel 258a exposed from the housing 250 via the opening portion 264. Consequently, the rack member 254 moves to the proximal side inside the housing 250 in accordance with rotations of the pinion 256a which is provided in the operation wheel 258a. Consequently, the outer tube 216, which is connected to the rack member 254 also moves in the proximal direction of the grip 218.

As a result thereof, in accordance with a movement of the outer tube 216 in the proximal direction with respect to the inner tube 214, the stent 212 which is accommodated inside the outer tube 216 (refer to FIG. 9) begins to be gradually exposed from the distal end side and begins to expand radially outward at the same time. In accordance with an exemplary embodiment, the stent 212 is released in accordance with a movement of the outer tube 216 in the proximal direction. Note that, when it is intended to adjust a position of the stent 212 inside a living body lumen at a stage where the stent 212 is released partway, the operation wheel 258a may be rotatively operated in the reverse direction (the arrow B direction). In this manner, the outer tube 216 moves in the distal end direction so that the stent 212 can be contained again inside the outer tube 216.

When the rack member 254 moves in the proximal direction in accordance with a rotative operation of the operation wheel 258a, as illustrated in FIG. 12B, the rack 255 of the rack member 254 eventually meshes with the pinion 256b which is provided right next thereto on the proximal side. In this case, the stent 212 is in a state of being released partway (approximately one third of the overall length). When the rack 255 of the rack member 254 meshes with the pinion 256b, the outer tube 216 is moved in the proximal direction so that the stent 212 is released further by rotatively operating the operation wheel 258b provided with the pinion 256b in a predetermined direction (the direction A).

Note that, when the pinion 256b provided in the operation wheel 258b right next thereto on the proximal side meshes with the rack member 254 while the operation wheel 258a is rotatively operated, the operation wheel 258b rotates while being interlocked therewith. Accordingly, a user can recognize that the rack 255 of the rack member 254 meshes with the pinion 256b. In addition, when the rack member 254 moves in the proximal direction in accordance with a rotative operation of the operation wheel 258a, the meshed state between the pinion 256a and the rack 255 is cancelled so that the operation wheel 258a rotates with no traction.

Therefore, a user can recognize that the rack member 254 meshes with the next pinion 256b and can recognize that the next operation wheel 258b is to be operated. In addition, when the grip 218 is provided with the position recognizing means, which can allow a position of the rack member 254 to be visually recognizable, a user can recognize that the rack member 254 meshes with the next pinion 256b by confirming the position of the rack member 254. Therefore, the user can recognize that the next operation wheel 258b is to be operated.

When the rack member 254 moves in the proximal direction in accordance with a rotative operation of the operation wheel 258b, as illustrated in FIG. 12C, the rack 255 of the rack member 254 eventually meshes with the pinion 256c which is provided right next thereto on the proximal side. In this case, the stent 212 is t in a state of being released partway (approximately two third of the overall length). When the rack 255 of the rack member 254 meshes with the pinion 256c, the outer tube 216 is moved in the proximal direction so that the stent 212 is released further by rotatively operating the operation wheel 258c provided with the pinion 256c in a predetermined direction (the direction A).

Then, the stent 212 is in a state of being completely exposed to the outer tube 216 (a state where the overall length of the stent 212 is released). In this manner, the stent 212 indwells in a lesion in a cylindrically dilated state.

Thereafter, the inner tube 214 and the outer tube 216 configuring the stent delivery system 210 are pulled to the proximal side so that the inner tube 214 and the outer tube 216 are removed from a living body while leaving only the stent 212 inside a living body lumen.

As described above, according to the stent delivery system 210 of the fifth embodiment of the present disclosure, the rack member 254 can be continuously moved in the proximal direction by the plurality of pinions 256 (256a to 256c), which are provided at interval from each other along the extension direction of the rack member 254. Therefore, the length L8 of the rack member 254 is quite shorter than the necessary movement distance L10 of the rack member 254 (refer to FIG. 12A). In contrast, in a case of a conventional configuration in which a rack member is moved by one pinion, since the length of the rack member needs to be set to be at least equal to or greater than the necessary movement distance thereof, the length of the rack member becomes quite long so that a grip which accommodates the rack member becomes unavoidably long as well.

In this manner, according to the stent delivery system 210, even in a case of a configuration in which a long stent 212 is released, the necessary movement distance L10 of the rack member 254 can be ensured without elongating the overall length of the rack member 254. Therefore, the length of the grip 218 can be shortened to the shortened length of the rack member 254, and the tractability of the grip 218 during a procedure can be improved.

In addition, the rack member 254 is provided in the grip 218. However, as described above, the stent delivery system 210 may have a configuration in which a position of the rack member 254 is visually recognizable from the outside of the grip 218. In a case of the aforementioned configuration, the timing of changing the pinion 256 can be easily known, that is, the operation wheel 258 to be rotated, and a procedure of releasing the stent 212 can be performed through an efficient operation.

Note that, in the embodiment described above, the rack member 254 is exemplified as a displacement member which moves in the axial direction of the grip 218, and the plurality of pinions 256 are exemplified as a plurality of driving rotators. However, the displacement member and the driving rotators are not limited to a configuration in which the rack 255 meshes with the pinions 256 so as to transmit power. For example, a configuration in which power is transmitted due to friction resistance caused by contact between an outer side surface of the displacement member and the outer circumferential surface of each of the driving rotators may be applied thereto. The aforementioned point is similarly applied to the sixth to seventh embodiments described below.

FIGS. 13A to 13C are schematic views illustrating a stent delivery system 210a according to a modification example. Note that, the grip 218 is illustrated in a simplified manner in FIGS. 13A to 13C. However, similar to the grip 218 illustrated in FIG. 9, the grip 218 has a shape which is suitable to be gripped, and a plurality of operation wheels 258 (258d and 258e) are partially exposed from the grip 218.

In the stent delivery system 210a according to the aforementioned modification example, a plurality of (two in the illustrated example) stents 212 (212a and 212b) are arranged side by side along the axial direction of the inner tube 214 and the outer tube 216.

In addition, the stent delivery system 210a is provided with a movement mechanism 252a for moving the outer tube 216 in the proximal direction with respect to the inner tube 214. A plurality of the operation wheels 258 in the same number as that of the stents 212, that is, for example, two in the present modification example are provided in the movement mechanism 252a. The operation wheels 258 are respectively provided with the pinions 256 (256d and 256e) which can mesh with the rack member 254. In the stent delivery system 210a, every time the pinions 256 rotate in order from the pinion on the distal side, the stents 212 are released from the outer tube 216 in order from the stent on the distal side.

In accordance with an exemplary embodiment, for example, as illustrated in FIG. 13A, when the rack member 254 is at the initial position (the position on the farthest distal end within the movable range), all of the stents 212 are contained in the outer tube 216 in a contracted state. When the pinion 256d is rotated by rotatively operating the first operation wheel 258d and the outer tube 216 is moved in the proximal direction together with the rack member 254 with respect to the inner tube 214, the first stent 212a is released from the outer tube 216. Then, as illustrated in FIG. 13B, the first stent 212a is completely released from the outer tube 216 at a stage where the rack member 254 moves rearward to a predetermined position. In this case, since the rack 255 of the rack member 254 does not mesh with the pinion 256d provided in the first operation wheel 258d, the operation wheels 258d rotates with no traction even though the operation wheels 258d is rotatively operated any further.

The rack 255 of the rack member 254 meshes with the pinion 256e which is provided in the second operation wheel 258e at a stage where the first stent 212a is released. Therefore, subsequently, the outer tube 216 is moved in the proximal direction together with the rack member 254 with respect to the inner tube 214 in accordance with a rotation of the pinion 256e by rotatively operating the second operation wheel 258e. Accordingly, as illustrated in FIG. 13C, the second stent 212b is released from the outer tube 216.

Note that, two of the stents 212a and 212b may be continuously released without changing a position of the stent delivery system 210a (the distal end of the inner tube 214). Otherwise, the position of the stent delivery system 210a (the distal end of the inner tube 214) may be changed and the second stent 212b may be released at a different place inside a living body lumen after the first stent 212a is released.

In the stent delivery system 210a, three or more stents 212 may be arranged side by side along the axial direction. In this case, three or more pinions 256 and the operation wheels 258 in the same number as that of the stents 212 are provided, and the stents 212 are continuously released from the outer tube 216 every time the operation wheels 258 are rotatively operated.

According to the stent delivery system 210a of the modification example, the rack member 254 is continuously moved in the proximal direction by the plurality of pinions 256 which are provided at intervals from each other along the extension direction of the rack member 254. According to the aforementioned configuration, the overall length of the rack member 254 can be shortened compared to a conventional configuration in which a rack member is moved by one pinion. Accordingly, even in a case of a configuration having the plurality of stents 212 arranged side by side in the axial direction to be released, the necessary movement distance L10 of the rack member 254 can be ensured without elongating the overall length of the rack member 254. Therefore, the length of the grip 218 can be shortened to the shortened length of the rack member 254, and the tractability of the grip 218 during a procedure can be improved.

FIG. 14 is a partially omitted side view of a stent delivery system 270 according to the sixth embodiment of the present disclosure. In FIG. 14, the proximal portion of the inner tube 214 and a grip 272 (the housing 250) are indicated by a virtual line. Note that, in the stent delivery system 270 according to the sixth embodiment, the same reference numbers are applied to elements exhibiting the function and the effect which are the same as or similar to those of the stent delivery system 210 according to the fifth embodiment, and detailed description thereof will be omitted.

The stent delivery system 270 is provided with the grip 272 having a movement mechanism 252b for moving the outer tube 216 in the proximal direction with respect to the inner tube 214. The movement mechanism 252b has the rack member 254, a plurality of pinions 282 and 284, a plurality of operation wheels 278 and 280 (the rotative operation portions). The rack member 254 is provided with a first rack 274 (a first driven portion) and a second rack 276 (a second driven portion) on sides opposite to each other (the upper side and the lower side in the illustrated example).

The plurality of operation wheels 278 and 280 have a plurality of (two in the illustrated example) rotatable first operation wheels 278 (the first rotative operation portions) which are arranged at intervals in the extension direction (in the axial direction) of the rack member 254, and a plurality of (three in the illustrated example) rotatable second operation wheels 280 (the second rotative operation portions) which are arranged at intervals in the extension direction (in the axial direction) of the rack member 254.

The plurality of first operation wheels 278 (278a and 278b) and the plurality of second operation wheels 280 (280a to 280c) are exposed on the outer side surfaces (the top surface and the bottom surface in FIG. 14) of the grip 272 on sides opposite to each other. In accordance with an exemplary embodiment, for example, the plurality of opening portions 264 corresponding to the plurality of first operation wheels 278 are provided on the top surface of the grip 272, and the first operation wheels 278 are partially and respectively exposed via the opening portions 264. In addition, the plurality of opening portions 264 corresponding to the plurality of second operation wheels 280 are provided on the bottom surface of the grip 272, and the second operation wheels 280 are partially and respectively exposed via the opening portions 264.

The first operation wheels 278 are respectively provided with first pinions 282 (the driving rotators) which can mesh with the first rack 274. The lengths (the lengths of the first rack 274 and the second rack 276) L8 of the rack member 254 are greater than a center-to-center distance L11 between the first pinions 282. The second operation wheels 280 are respectively provided with second pinions 284 (the driving rotators) which can mesh with the second rack 276. The lengths L8 of the rack members 254 are greater than a center-to-center distance L12 between the second pinions 284. The rack members 254 mesh with at least one of the first pinions 282 and mesh with at least one of the second pinions 284 within the movable ranges of the rack members 254.

In the present embodiment, the product of the number of teeth and the module of each second pinion 284 is greater than the product of the number of teeth and the module of each first pinion 282. Therefore, a movement distance per unit rotation angle of each second pinion 284 in the rack member 254 is greater than a movement distance per unit rotation angle of each first pinion 282 in the rack member 254. In other words, when the rotation angles thereof are the same as each other, the movement distance of the rack member 254 driven by the second pinions 284 is greater than the movement distance of the rack member 254 driven by the first pinions 282.

Accordingly, in a case where a rotative operation speed with respect to first operation wheels 278 and a rotative operation speed with respect to second operation wheels 280 are the same as each other, when the first operation wheels 278 are rotatively operated, the movement speed of the outer tube 216 which moves together with the rack member 254 is relatively slow. When the second operation wheels 280 are rotatively operated, the movement speed of the outer tube 216, which moves together with the rack member 254 can be relatively fast.

Note that, the numbers of teeth and the modules are the same as each other in the plurality of first pinions 282 (282a and 282b), and the numbers of teeth and the modules are the same as each other in the plurality of second pinions 284 (284a to 284c). The modules of the first pinions 282 and the second pinions 284 may be the same as each other. However, in this case, as illustrated in FIG. 14, the number of teeth of each second pinion 284 is greater than the number of teeth of each first pinion 282. Otherwise, the number of teeth of each first pinion 282 and the number of teeth of each second pinion 284 may be the same as each other, and the module of each second pinion 284 may be greater than the module of each first pinion 282. Moreover, the number of teeth and the module of each second pinion 284 may be respectively greater than the number of teeth and the module of each first pinion 282.

According to the stent delivery system 270 having the aforementioned configuration, when the first operation wheels 278 or the second operation wheels 280 are rotatively operated in order from that on the distal side, the plurality of pinions 282 and 284 rotate so that the rack member 254 is moved continuously in the proximal direction. Thus, the outer tube 216 can be moved in the proximal direction with respect to the inner tube 214. At a stage where the stent 212 is gradually released from the distal side thereof in accordance with a movement of the outer tube 216 in the proximal direction and the rack member 254 is moved to a position depicted with the dotted line in FIG. 14, the stent 212 is completely released from the distal end of the outer tube 216.

In this case, the first pinion 282 and the second pinion 284 are different from each other in speed of moving the rack member 254. Therefore, a release speed of the stent 212 from the outer tube 216 can be easily controlled by rotatively operating the first operation wheels 278 or the second operation wheels 280 so as to rotate the first pinion 282 or the second pinion 284 in accordance with an intended speed of releasing the stent 212.

For example, when the stent 212 is intended to be slowly released, the first operation wheels 278 may be rotatively operated so as to cause the first pinions 282 having less teeth to drive the rack member 254. Then, the outer tube 216 is moved in the proximal direction at a low speed. Meanwhile, when the stent 212 is intended to be promptly released, the second operation wheels 280 may be rotatively operated so as to cause the second pinions 284 having more teeth to drive the rack member 254. Then, the outer tube 216 moves in the proximal direction at a high speed.

In addition, for example, in a case of a long stent 212, the first operation wheel 278a on the distal side is rotatively operated so as to cause the first pinion 282a to drive the rack member 254 at the initial stage of releasing the stent 212. Then, the outer tube 216 is moved in the proximal direction. Consequently, the stent 212 is slowly released, thereby being easy to be positioned. Meanwhile, the second operation wheel 280c on the proximal side is rotatively operated so as to cause the second pinion 284c to drive the rack member 254 at the final stage of releasing the stent 212. Then, the outer tube 216 is moved in the proximal direction. Consequently, the stent 212 is promptly released. Thus, the procedure can end early.

Similar to the fifth embodiment, in the sixth embodiment as well, the rack member 254 is driven by the plurality of pinions 282 and 284 which are arranged at intervals in the extension direction of the rack member 254. Therefore, the rack member 254 can have a quite short length L8 compared to the necessary movement distance L10 of the rack member 254. Accordingly, even in a case of a configuration having a long stent 212 or the plurality of stents 212a and 212b (refer to FIGS. 13A to 13C) arranged side by side in the axial direction to be released, there is no need to increase the rack member 254 in length and size. As a result thereof, the length of the grip 272 can be shortened and the tractability of the grip 272 during a procedure can be improved.

In addition, according to the present embodiment, the first pinion 282 and the second pinion 284 are different from each other in speed of moving the rack member 254. Therefore, a release speed of the stent 212 from the outer tube 216 can be easily controlled by rotating the first pinions 282 or the second pinions 284 in accordance with an intended speed of releasing the stent 212.

In addition, according to the present embodiment, since the first pinions 282 and the second pinions 284 are arranged on sides opposite to each other while having the rack member 254 as a reference, the first pinions 282 and the second pinions 284 which are respectively provided to be plural in number can be efficiently arranged inside the grip 272.

Furthermore, according to the present embodiment, since the first operation wheels 278 and the second operation wheels 280 are exposed from the grip 272 on sides different from each other, it can be relatively easy for a user to discriminate between the first operation wheels 278 and the second operation wheels 280, which are thereby suitably and easily used.

Moreover, in the sixth embodiment, it is natural for each of the configuration portions in common with that of the fifth embodiment to be able to attain the operation and the effect which are the same as or similar to the operation and the effect of each of the configuration portions of the fifth embodiment in common.

Note that, in the configuration illustrated in FIG. 14, the product of the number of teeth and the module of each second pinion 284 is greater than the product of the number of teeth and the module of each first pinion 282. However, in contrast with the aforementioned configuration, the product of the number of teeth and the module of each first pinion 282 may be greater than the product of the number of teeth and the module of each second pinion 284. In this case, the stent 212 can be promptly released when the first operation wheels 278 provided with the first pinions 282 are rotatively operated, and the stent 212 is slowly released when the second operation wheels 280 provided with the second pinions 284 are rotatively operated.

In addition, in the configuration illustrated in FIG. 14, two racks (the first rack 274 and the second rack 276) are provided in the rack member 254, and the plurality of first pinions 282 and the plurality of second pinions 284 are arranged on sides opposite to each other. However, the configuration may have the below-described arrangement. In other words, only one rack may be provided in the rack member 254, and the plurality of first pinions 282 and the plurality of second pinions 284 may be provided on the same side with respect to the rack member 254. In this case, the plurality of first pinions 282 and the plurality of second pinions 284 are alternately arranged along the axial direction of the rack member 254.

FIG. 15 is a partially omitted side view of a stent delivery system 290 according to the seventh embodiment of the present disclosure. In FIG. 15, the proximal portion of the inner tube 214 and a grip 292 (the housing 250) are indicated by a virtual line. Note that, in the stent delivery system 290 according to the seventh embodiment, the same reference numbers are applied to elements exhibiting the function and the effect which are the same as or similar to those of the stent delivery system 210 according to the fifth embodiment, and detailed description thereof will be omitted.

The stent delivery system 290 is provided with the grip 292 which has a movement mechanism 252c for moving the outer tube 216 in the proximal direction with respect to the inner tube 214. The movement mechanism 252c has the rack member 254, a plurality of (three in the illustrated example) pinions 299, and a plurality of (three in the illustrated example) operation wheels 294. The rack member 254 is provided with the first rack 274 and the second rack 276 on sides opposite to each other (the upper side and the lower side in the illustrated example).

The plurality of operation wheels 294 are rotatably arranged at intervals in the extension direction (in the axial direction) of the rack member 254. The plurality of operation wheels 294 include first operation wheels 296 which drive the rack member 254 via the first rack 274, and a second operation wheel 298 which drives the rack member 254 via the second rack 276. In the illustrated example, two first operation wheels 296 are provided, and one second operation wheel 298 is provided.

The first operation wheels 296 and the second operation wheel 298 are exposed on the outer side surface (the top surface and the bottom surface in FIG. 15) of the grip 292 on sides opposite to each other. In accordance with an exemplary embodiment, for example, the plurality of opening portions 264 corresponding to the plurality of first operation wheels 296 are provided on the top surface of the grip 292, and the first operation wheels 296 are partially and respectively exposed via the opening portions 264. In addition, the opening portion 264 corresponding to the second operation wheel 298 is provided on the bottom surface of the grip 292, and the second operation wheel 298 is partially exposed via the opening portion 264.

The first operation wheels 296 are respectively provided with first pinions 300 which can mesh with the first rack 274. The second operation wheel 298 is provided with a second pinion 302, which can mesh with the second rack 276. The product of the number of teeth and the module of the second pinion 302 can be greater than the product of the number of teeth and the module of each first pinion 300. Therefore, a movement distance per unit rotation angle of the second pinion 302 in the rack member 254 is greater than a movement distance per unit rotation angle of each first pinion 300 in the rack member 254. In other words, when the rotation angles thereof are the same as each other, the movement distance of the rack member 254 driven by the second pinion 302 is greater than the movement distance of the rack member 254 driven by each first pinion 300.

Accordingly, in a case where a rotative operation speed with respect to each first operation wheel 296 and a rotative operation speed with respect to the second operation wheel 298 are the same as each other, when the first operation wheels 296 are rotatively operated, the movement speed of the outer tube 216 which moves together with the rack member 254 is relatively slow. When the second operation wheel 298 is rotatively operated, the movement speed of the outer tube 216 which moves together with the rack member 254 is relatively fast.

The numbers of teeth and the modules are the same as each other in the plurality of first pinions 300. The modules of each first pinion 300 and the second pinion 302 may be the same as each other. However, in this case, as illustrated in FIG. 15, the number of teeth of the second pinion 302 is greater than the number of teeth of each first pinion 300. Otherwise, the number of teeth of each first pinion 300 and the number of teeth of the second pinion 302 may be the same as each other, and the module of the second pinion 302 may be greater than the module of each first pinion 300. Moreover, the number of teeth and the module of the second pinion 302 may be respectively greater than the number of teeth and the module of each first pinion 300.

The lengths (the lengths of the racks 274 and 276) L8 of the rack member 254 are greater than a center-to-center distance L13 between the first pinions 300. In addition, the length L8 of the rack member 254 is greater than a center-to-center distance L14 between the first pinion 300 on the proximal side and the second pinion 302. Accordingly, the rack member 254 meshes with at least two adjacent pinions among the plurality of pinions 300 and 302 in the axial direction of the grip 292 (in the extension direction of the rack member 254) within the movable ranges of the rack members 254. Note that, the center-to-center distance L13 between the first pinions 300, and the center-to-center distance L14 between the first pinion 300 on the proximal side and the second pinion 302 may be the same as each other or may be different from each other.

According to the stent delivery system 290 having the aforementioned configuration, when the plurality of operation wheels 294 are rotatively operated in order from that on the distal side, the plurality of pinions 300 and 302 rotate so that the rack member 254 is moved continuously in the proximal direction. Thus, the outer tube 216 can be moved in the proximal direction with respect to the inner tube 214. At a stage where the stent 212 is gradually released from the distal end side thereof in accordance with a movement of the outer tube 216 in the proximal direction and the rack member 254 is moved to a position depicted with the dotted line in FIG. 15, the stent 212 is completely released from the distal end of the outer tube 216.

In this case, the first operation wheel 296 is rotatively operated so as to cause the first pinion 300 on the distal side to move the rack member 254 at a low speed in the proximal direction at the initial stage of releasing the stent 212. Therefore, the stent 212 is slowly released, thereby being easy to be positioned. In this manner, the first pinion 300 on the distal side functions as a driving rotator for performing release at the initial stage in which the rack member 254 is moved at the initial stage of releasing the stent 212.

Meanwhile, the second operation wheel 298 is rotatively operated so as to cause the second pinion 302 to move the rack member 254 at a high speed in the proximal direction at the final stage of releasing the stent 212. Therefore, the stent 212 is promptly released. Thus, the procedure can end early. In this manner, the second pinion 302 functions as a driving rotator for performing release at the final stage in which the rack member 254 is moved at the final stage of releasing the stent 212.

Similar to the fifth embodiment, in the seventh embodiment as well, the rack member 254 is driven by the plurality of pinions 300 and 302 which are arranged at intervals in the extension direction of the rack member 254. Therefore, the rack member 254 can have a quite short length L8 compared to the necessary movement distance L10 of the rack member 254. Accordingly, even in a case of a configuration having a long stent 212 or the plurality of stents 212a and 212b (refer to FIGS. 13A to 13C) arranged side by side in the axial direction to be released, there is no need to increase the rack member 254 in length and size. As a result thereof, the length of the grip 292 can be shortened and the tractability of the grip 292 during a procedure can be improved.

In addition, according to the present embodiment, since the first operation wheels 296 and the second operation wheel 298 are exposed from the grip 292 on sides different from each other, it can be easy for a user to discriminate between the first operation wheels 296 and the second operation wheel 298, which are thereby suitably and easily used.

Moreover, in the seventh embodiment, it is natural for each of the configuration portions in common with that of the fifth embodiment to be able to attain the operation and the effect which are the same as or similar to the operation and the effect of each of the configuration portions of the fifth embodiment in common.

In the configuration illustrated in FIG. 15, two racks (the first rack 274 and the second rack 276) are provided in the rack member 254, and the first pinion 300 and the second pinion 302 are arranged on sides opposite to each other in the rack member 254. However, the configuration may have the below-described arrangement. In other words, only one rack may be provided in the rack member 254, and the first pinion 300 and the second pinion 302 may be provided on the same side with respect to the rack member 254.

Hereinbefore, the embodiments suitable for the present disclosure are described. However, it is not necessary to mention that the present disclosure is not limited to the embodiments described above and the present disclosure can be variously modified and changed without departing from the scope of the gist of the present disclosure.

The detailed description above describes a stent delivery system in which a stent is delivered to the inside of a living body lumen such as a blood vessel and the like and indwells therein. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
an inner member;
a sheath that is arranged outside the inner member so as to be movable in an axial direction with respect to the inner member;
a self-expandable stent that is arranged between the inner member and the sheath;
a grip that includes a movement mechanism for moving the sheath in the axial direction with respect to the inner member,
wherein the stent is contained in the sheath in an initial state, and the stent is configured to be released inside a living body lumen in accordance with a movement of the sheath in a proximal direction with respect to the inner member, and
wherein the movement mechanism has a displacement member which is connected to the sheath, wherein the displacement member is movable along the axial direction of the stent delivery system and extends in the axial direction; and
a plurality of driving rotators which are arranged at intervals from each other in an extension direction of the displacement member, and move the displacement member in the extension direction in accordance with rotations of the plurality of driving rotators, and wherein the plurality of driving rotators are three or more.

2. The stent delivery system according to claim 1, further comprising:
an interlocking mechanism that interlocks the plurality of driving rotators with each other; and
a rotative operation portion that rotates the plurality of driving rotators via the interlocking mechanism.

3. The stent delivery system according to claim 2, wherein one of the plurality of driving rotators is provided in the rotative operation portion.

4. The stent delivery system according to claim 2, wherein the interlocking mechanism has a plurality of rotative portions which are coaxially and respectively provided in the plurality of driving rotators, and at least one transmission member which comes into contact with the plurality of rotative portions so as to be able to transmit power to the plurality of rotative portions.

5. The stent delivery system according to claim 4, wherein when the plurality of rotative portions are interlocked with each other by the transmission member, a rotative portion on a farthest proximal side rotates faster than a rotative portion on a farthest distal side.

6. The stent delivery system according to claim 1, wherein a plurality of the stents are arranged side by side along the axial direction of the inner member,
wherein a number of the driving rotators is a same as a number of the stents, and wherein every time the driving rotators rotate in order from the driving rotator on a distal side, the stents are released from the sheath in order from the stent on the distal side.

7. The stent delivery system according to claim 1, wherein at least one of the driving rotators is different from the remaining driving rotators in a movement distance per unit rotation angle of each of the driving rotators in the displacement member.

8. The stent delivery system according to claim 1, wherein a position of the displacement member is visually recognizable from the outside of the grip.

9. A stent delivery system comprising:
an inner member;
a sheath that is arranged outside the inner member so as to be movable in an axial direction with respect to the inner member;
a self-expandable stent that is arranged between the inner member and the sheath;
a grip that includes a movement mechanism for moving the sheath in the axial direction with respect to the inner member,
wherein the stent is contained in the sheath in an initial state, and the stent is configured to be released inside a living body lumen in accordance with a movement of the sheath in a proximal direction with respect to the inner member, and
wherein the movement mechanism has a displacement member which is connected to the sheath, wherein the displacement member is movable along the axial direction of the stent delivery system and extends in the axial direction;
a plurality of driving rotators which are arranged at intervals from each other in an extension direction of the displacement member, and move the displacement member in the extension direction in accordance with rotations of the plurality of driving rotators;
an interlocking mechanism that interlocks the plurality of driving rotators with each other; and
a rotative operation portion that rotates the plurality of driving rotators via the interlocking mechanism,
wherein the plurality of driving rotators include a plurality of first driving rotators and a plurality of second driving rotators,
wherein at least one of the plurality of first driving rotators and at least one of the plurality of second driving rotators are configured to drive the displacement member within a movable range of the displacement member,
wherein the interlocking mechanism has a first interlocking portion which interlocks the plurality of first driving rotators with each other, and a second interlocking portion which interlocks the plurality of second driving rotators with each other, and
wherein a movement distance per unit rotation angle of each of the plurality of first driving rotators in the displacement member is different from a movement distance per unit rotation angle of each of the plurality of second driving rotators in the displacement member.

10. The stent delivery system according to claim 9, wherein the first interlocking portion has a plurality of first rotative portions which are coaxially and respectively provided in the plurality of first driving rotators, and at least one first transmission member which comes into contact with the plurality of first rotative portions so as to be able to transmit power to the plurality of first rotative portions, and wherein the second interlocking portion has a plurality of second rotative portions which are coaxially and respectively provided in the plurality of second driving rotators and at least one second transmission member which comes into contact with the plurality of second rotative portions so as to be able to transmit power to the plurality of second rotative portions.

11. The stent delivery system according to claim 10, wherein the displacement member has first and second driven portions on sides opposite to each other,
wherein the plurality of first driving rotators abut on the first driven portion and drive the displacement member, and
wherein the plurality of second driving rotators abut on the second driven portion and drive the displacement member.

12. The stent delivery system according to claim 11, wherein one of the plurality of first driving rotators is provided in a first rotative operation portion which is rotatably supported by the grip,
wherein one of the plurality of second driving rotators is provided in a second rotative operation portion which is rotatably supported by the grip, and
wherein the first rotative operation portion and the second rotative operation portion are exposed on outer side surfaces of the grip on sides opposite to each other.

13. A stent delivery system comprising:
an inner member;
a sheath that is arranged outside the inner member so as to be movable in an axial direction with respect to the inner member;
a self-expandable stent that is arranged between the inner member and the sheath;
a grip that includes a movement mechanism for moving the sheath in the axial direction with respect to the inner member,
wherein the stent is contained in the sheath in an initial state, and the stent is configured to be released inside a living body lumen in accordance with a movement of the sheath in a proximal direction with respect to the inner member, and
wherein the movement mechanism has a displacement member which is connected to the sheath, wherein the displacement member is movable along the axial direction of the stent delivery system and extends in the axial direction; and
a plurality of driving rotators which are arranged at intervals from each other in an extension direction of the displacement member, and move the displacement member in the extension direction in accordance with rotations of the plurality of driving rotators,
wherein the plurality of driving rotators include a plurality of first driving rotators and a plurality of second driving rotators,
wherein at least one of the plurality of first driving rotators and at least one of the plurality of second driving rotators are able to drive the displacement member at all times within a movable range of the displacement member, and
wherein a movement distance per unit rotation angle of each of the plurality of first driving rotators in the displacement member is different from a movement distance per unit rotation angle of each of the plurality of second driving rotators in the displacement member.

14. The stent delivery system according to claim 13, wherein the displacement member has first and second driven portions on sides opposite to each other, wherein the plurality of first driving rotators abut on the first driven portion and drive the displacement member, and wherein the plurality of second driving rotators abut on the second driven portion and drive the displacement member.

15. The stent delivery system according to claim 14, wherein the first driving rotators are respectively provided in a plurality of first rotative operation portions which are rotatably supported by the grip, wherein the second driving rotators are respectively provided in a plurality of second rotative operation portions which are rotatably supported by the grip, and wherein the plurality of first rotative operation portions and the plurality of second rotative operation portions are respectively exposed on outer side surfaces of the grip on sides opposite to each other.

16. A stent delivery system comprising:

an inner member;

a sheath that is arranged outside the inner member so as to be movable in an axial direction with respect to the inner member;

a self-expandable stent that is arranged between the inner member and the sheath;

a grip that includes a movement mechanism for moving the sheath in the axial direction with respect to the inner member, wherein the stent is contained in the sheath in an initial state, and the stent is configured to be released inside a living body lumen in accordance with a movement of the sheath in a proximal direction with respect to the inner member, and wherein the movement mechanism has a displacement member which is connected to the sheath, wherein the displacement member is movable along the axial direction of the stent delivery system and extends in the axial direction; and a plurality of driving rotators which are arranged at intervals from each other in an extension direction of the displacement member, and move the displacement member in the extension direction in accordance with rotations of the plurality of driving rotators, wherein a movement distance per unit rotation angle of the driving rotator provided on a farthest proximal side in the displacement member is greater than a movement distance per unit rotation angle of the driving rotator provided on a farthest distal side in the displacement member.

17. The stent delivery system according to claim 16, wherein the driving rotator provided on the farthest distal side is provided in a first rotative operation portion which is rotatably supported by the grip, wherein the driving rotator provided on the farthest proximal side is provided in a second rotative operation portion which is rotatably supported by the grip, and wherein the first rotative operation portion and the second rotative operation portion are exposed on outer side surfaces of the grip on sides opposite to each other.

18. The stent delivery system according to claim 16, further comprising:

an interlocking mechanism that interlocks the plurality of driving rotators with each other; and a rotative operation portion that rotates the plurality of driving rotators via the interlocking mechanism.

19. The stent delivery system according to claim 18, wherein the interlocking mechanism has a plurality of rotative portions which are coaxially and respectively provided in the plurality of driving rotators, and at least one transmission member which comes into contact with the plurality of rotative portions so as to be able to transmit power to the plurality of rotative portions.

20. The stent delivery system according to claim 19, wherein when the plurality of rotative portions are interlocked with each other by the transmission member, a rotative portion on a farthest proximal side rotates faster than a rotative portion on a farthest distal side.

* * * * *